US006864049B1

(12) United States Patent
Nguyen et al.

(10) Patent No.: US 6,864,049 B1
(45) Date of Patent: Mar. 8, 2005

(54) METHOD FOR PRODUCING HYBRIDIZATION COMPLEXES WHOSE STABILITY IS SUBSTANTIALLY INDEPENDENT OF THE BASE COMPOSITION OF TWO HYBRIDIZED NUCLEIC ACID MOLECULES

(75) Inventors: Thuong Nguyen, Vienne en Val (FR); Ulysse Asseline, Orléans (FR); Hong Khanh Nguyen, Vienne en Val (FR); Maurice Durand, Orléans (FR); Jean-Claude Maurizot, Orléans (FR); Daniel Dupret, Haguenau (FR); Edwige Bonfils, Strasbourg (FR)

(73) Assignee: Appligene-Oncor S.A., Illkirch Cedex (FR)

( * ) Notice: Subject to any disclaimer, the term of this patent is extended or adjusted under 35 U.S.C. 154(b) by 0 days.

(21) Appl. No.: 09/214,403

(22) PCT Filed: Jun. 25, 1997

(86) PCT No.: PCT/FR97/01131

§ 371 (c)(1),
(2), (4) Date: Jul. 20, 1999

(87) PCT Pub. No.: WO97/49833

PCT Pub. Date: Dec. 31, 1997

(30) Foreign Application Priority Data

Jun. 27, 1996 (FR) .............................. 96 08027

(51) Int. Cl.[7] .................... C12Q 1/68; C12N 15/11
(52) U.S. Cl. ........................................ 435/6; 536/24.3
(58) Field of Search ............................. 435/6; 536/24.3

(56) References Cited

U.S. PATENT DOCUMENTS 5,844,110 A * 12/1998 Gold ........................ 536/22.1

FOREIGN PATENT DOCUMENTS

WO    WO 93 05175    3/1993

OTHER PUBLICATIONS

Melchior W.B. et al., "Alteration of the Relative Stability of DA.DT and DG.DC Base Pairs in DNA," *Proceedings of the National Academy of Sciences of the USA*, vol. 70, No. 2, pp. 298–302, Feb. 1973.

Wood W. I. et al., "Base Composition–Independent Hybridization in Tetramethylammonium Chloride: A Method for Oligonucleotide Screening of Highly Complex Gene Libraries," *Proceedings of the National Academy of Sciences of USA*, vol. 82, No. 3, pp. 1585–1588, Mar. 3, 1985.

Nguyen H–K, et al., "Studies Towards the Design of a Modified GC Base Pair with Stability Similar to that of the AT Base Pair," *Tetrahedron Letters*, vol. 38, No. 23, pp. 4083–4086, Jun. 9, 1997.

Nguyen H., et al., "Modification of DNA Duplexes to Smooth Their thermal Stability Independently of Their Base Content for DNA Sequencing by Hybridization," *Nucleic Acids Research*, vol. 25, No. 15, pp. 3059–3065, Aug. 1, 1997.

* cited by examiner

*Primary Examiner*—John S. Brusca
(74) *Attorney, Agent, or Firm*—Hoffmann & Baron, LLP; Irving Feit

(57) ABSTRACT

The invention discloses a method for producing a hybridization complex whose stability is substantially independent of the base composition of two hybridized nucleic acid molecules, consisting in contacting a first nucleic acid molecule with a second nucleic acid molecule under conditions enabling the formation of a specific hybridization complex. The invention is characterized in that at least one of the four types of bases contained in the sequence of the first and/or of the second nucleic acid molecule is a modified base having pairing properties close to those of the natural base it replaces, such that at least one of the two types of the base pair contained in the composition of the complex comprises a modified base and in that the totality of the base pairs contained in the composition of the said complex has a like stability.

31 Claims, 13 Drawing Sheets

FIG. 1

| Duplex | | | | | | | | | | | | *Tm(°C) |
|---|---|---|---|---|---|---|---|---|---|---|---|---|
| 1 | 5' T T | T | C | G | T | C | A | T | C | G | T T 3' | 46.1 |
|   | 3' A | A | G | C | A | G | T | A | G | C | 5' |   |
|   |   | 9 | 8 | 7 | 6 | 5 | 4 | 3 | 2 | 1 |   |   |
| 2 | 5' T T | T | C | G | T | C | G | T | C | G | T T 3' | 51.3 |
|   | 3' A | A | G | C | A | G | C | A | G | C | 5' |   |
| 3 | 5' T T | T | C | G | T | C | G | T | C | G | T T 3' | 49.2 |
|   |   | A | G | C | A | G | 4Me C | A | G | C |   |   |
| 4 | 5' T T | T | C | G | T | C | G | T | C | G | T T 3' | 47.2 |
|   |   | A | G | C | A | G | 4Et C | A | G | C |   |   |
| 5 | 5' T T | T | C | G | T | C | G | T | C | G | T T 3' | 45.1 |
|   |   | A | G | T | A | G | 4Pro C | A | G | C |   |   |
| 6 | 5' T T | T | C | G | T | C | G | T | C | G | T T 3' | 45.6 |
|   |   | A | G | C | A | G | 4Allyl C | A | G | C |   |   |
| 7 | 5' T T | T | C | G | T | C | G | T | C | G | T T 3' | 45.8 |
|   |   | A | G | C | A | G | 4Propargyl C | A | G | C |   |   |
| 8 | 5' T T | T | C | G | T | C | G | T | C | G | T T 3' | 48 |
|   |   | A | G | C | A | G | ara C | A | G | C |   |   |

FIG. 3

| Duplex | Sequence | *Tm(°C) |
|---|---|---|
| 14 | 5' T T T C G T C a T C G T T 3'<br>    3' A G C A G C A G C 5' | 26.8 |
| 15 | 5' T T T C G T C a T C G T T 3'<br>              4Me<br>        A G C A G [C] A G C | 27.1 |
| 16 | 5' T T T C G T C a T C G T T 3'<br>              4Et<br>        A G C A G [C] A G C | 25.7 |
| 17 | 5' T T T C G T C a T C G T T 3'<br>              4Pro<br>        A G T A G [C] A G C | 24 |
| 18 | 5' T T T C G T C a T C G T T 3'<br>              4Allyl<br>        A G C A G [C] A G C | 24.2 |
| 19 | 5' T T T C G T C a T C G T T 3'<br>              4Propargyl<br>        A G C A G [C] A G C | 24.2 |
| 20 | 5' T T T C G T C a T C G T T 3'<br>              ara<br>        A G C A G [C] A G C | 22.1 |

FIG. 4

| Duplex | | | | | | | | | | | | | *Tm(°C) |
|---|---|---|---|---|---|---|---|---|---|---|---|---|---|
| 21 | 5'<br>3' | T | T | T<br>A | C<br>G | G<br>C | T<br>A | C<br>G | c<br>C | T<br>A | C<br>G | G<br>C | T<br>5' | T | 3' | 21 |

| 22 | 5' | T | T | T | C | G | T | C | c | T | C | G | T | T | 3' |
|---|---|---|---|---|---|---|---|---|---|---|---|---|---|---|---|
|    |    |   |   |   |   |   |   |   | 4Me |   |   |   |   |   |   |
|    |    |   |   | A | G | C | A | G | C | A | G | C |   |   |   |

Tm = 17.3

| 23 | 5' T T  T C G T C c T C G  T T 3' |
4Et
A G C A G [C] A G C

Tm = 18

Duplex 24: 5' T T T C G T C c T C G T T 3' / 4Pro / A G T A G [C] A G C — Tm = 21.8

Duplex 25: 5' T T T C G T C c T C G T T 3' / 4Allyl / A G C A G [C] A G C — Tm = 19.6

Duplex 26: 5' T T T C G T C c T C G T T 3' / 4Propargyl / A G C A G [C] A G C — Tm = 20.6

Duplex 27: 5' T T T C G T C c T C G T T 3' / ara / A G C A G [C] A G C — Tm = 19.3

FIG. 5

| Duplex | | | | | | | | | | | | | *Tm(°C) |
|---|---|---|---|---|---|---|---|---|---|---|---|---|---|
| 28 | 5' T | T | T | C | G | T | C  t | t  T | C | G | T | T 3' | 28.3 |
|    |      | 3'| A | G | C | A | G  C | C  A | G | C |   | 5'    |      |

| 29 | 5' T | T | T | C | G | T | C | t       | T | C | G | T | T 3' | 24.7 |
|---|---|---|---|---|---|---|---|---|---|---|---|---|---|---|
|    |     |   |   |   |   |   |   | 4Me     |   |   |   |   |      |      |
|    |     |   | A | G | C | A | G | [C]     | A | G | C |   |      |      |

| 30 | 5' T | T | T | C | G | T | C | t    | T | C | G | T | T 3' | 20.7 |
|---|---|---|---|---|---|---|---|---|---|---|---|---|---|---|
|    |     |   |   |   |   |   |   | 4Et  |   |   |   |   |      |      |
|    |     |   | A | G | C | A | G | [C]  | A | G | C |   |      |      |

| 31 | 5' T | T | T | C | G | T | C | t    | T | C | G | T | T 3' | 21.6 |
|---|---|---|---|---|---|---|---|---|---|---|---|---|---|---|
|    |     |   |   |   |   |   |   | 4Pro |   |   |   |   |      |      |
|    |     |   | A | G | T | A | G | [C]  | A | G | C |   |      |      |

| 32 | 5' T | T | T | C | G | T | C | t     | T | C | G | T | T 3' | 20.2 |
|---|---|---|---|---|---|---|---|---|---|---|---|---|---|---|
|    |     |   |   |   |   |   |   | 4Allyl|   |   |   |   |      |      |
|    |     |   | A | G | C | A | G | [C]   | A | G | C |   |      |      |

| 33 | 5' T | T | T | C | G | T | C | t         | T | C | G | T | T 3' | 22.5 |
|---|---|---|---|---|---|---|---|---|---|---|---|---|---|---|
|    |     |   |   |   |   |   |   | 4Propargyl|   |   |   |   |      |      |
|    |     |   | A | G | C | A | G | [C]       | A | G | C |   |      |      |

| 34 | 5' T | T | T | C | G | T | C | t   | T | C | G | T | T 3' | 21.9 |
|---|---|---|---|---|---|---|---|---|---|---|---|---|---|---|
|    |     |   |   |   |   |   |   | ara |   |   |   |   |      |      |
|    |     |   | A | G | C | A | G | [C] | A | G | C |   |      |      |

FIG. 6

| Duplex | | | | | | | | | | | | | | *Tm(°C) |
|---|---|---|---|---|---|---|---|---|---|---|---|---|---|---|
| 35 | 5' | T | T | T | A | T | T | A | T | T | A | T | T T 3' | 20 |
|  |  |  | 3' | A | T | A | A | T | A | A | T | A | 5' |  |
| 36 | 5' | T | T | T | G | T | T | G | T | T | G | T | T T 3' | 41.2 |
|  |  |  | 3' | A | C | A | A | C | A | A | C | A | 5' |  |
|  |  |  |  | 9 | 8 | 7 | 6 | 5 | 4 | 3 | 2 | 1 |  |  |
| 37 | 5' | T | T | T | G | T | T | G | T | T | G | T | T T 3' | 27.4 |
|  |  |  |  |  | 4Et |  |  | 4Et |  |  | 4Et |  |  |  |
|  |  |  |  | A | C | A | A | C | A | A | C | A |  |  |
| 38 | 5' | T | T | T | C | G | T | t | G | T | C | G | T T 3' | <10 |
|  |  |  |  |  | 4Et |  |  | 4Et |  |  | 4Et |  |  |  |
|  |  |  |  | A | C | A | A | C | A | A | C | A |  |  |
| 39 | 5' | T | T | T | C | G | T | c | G | T | C | G | T T 3' | <10 |
|  |  |  |  |  | 4Et |  |  | 4Et |  |  | 4Et |  |  |  |
|  |  |  |  | A | C | A | A | C | A | A | C | A |  |  |
| 40 | 5' | T | T | T | C | G | T | a | G | T | C | G | T T 3' | <10 |
|  |  |  |  |  | 4Et |  |  | 4Et |  |  | 4Et |  |  |  |
|  |  |  |  | A | C | A | A | C | A | A | C | A |  |  |

FIG. 7

| Duplex | | | | | | | | | | | | | | *Tm(°C) |
|---|---|---|---|---|---|---|---|---|---|---|---|---|---|---|
| 28 | 5' T T | | T C | G | T C | T | T C | G | | T T 3' | | | | 28.3 |
|    |        3' | | A G | C | A G | C | A G | C | | 5' | | | | |
| 21 | 5' T T | | T C | G | T C | C | T C | G | | T T 3' | | | | 21 |
|    |        3' | | A G | C | A G | C | A G | C | | 5' | | | | |
| 14 | 5' T T | | T C | G | T C | A | T C | G | | T T 3' | | | | 26.8 |
|    |        3' | | A G | C | A G | C | A G | C | | 5' | | | | |
| 2  | 5' T T | | T C | G | T C | G | T C | G | | T T 3' | | | | 51.3 |
|    |        3' | | A G | C | A G | C | A G | C | | 5' | | | | |
| 41 | 5' T T | | T T | A | T T | A | T T | A | | T T 3' | | | | 18.7 |
|    |        3' | | A A | T | A A | T | A A | T | | 5' | | | | |

Duplex 42:
5' T T  T [C(4Me)] G T [C(4Me)] G T [C(4Me)] G  T T 3'
         A G [C(4Me)] A G [C(4Me)] A G [C(4Me)]
Tm = 29.8

Duplex 43:
5' T T  T [C(4Et)] G T [C(4Et)] G T [C(4Et)] G  T T 3'
         A G [C(4Et)] A G [C(4Et)] A G [C(4Et)]
Tm = 24

Duplex 44:
5' T T  T [C(4Et)] G T [C(4Et)] t T [C(4Et)] G  T T 3'
         A G [C(4Et)] A G [C(4Et)] A G [C(4Et)]
Tm = <10

FIG. 8

| Duplex | | | | | | | | | | | | | | *Tm(°C) |
|---|---|---|---|---|---|---|---|---|---|---|---|---|---|---|
| 41 | 5' | T | T | T | T | A | T | T | A | T | T | A | T T 3' | 18.7 |
|  |  |  | 3' | A | A | T | A | A | T | A | A | T | 5' |  |
| 45 | 5' | T | T | C | C | G | C | C | G | C | C | G | T T 3' | 63.4 |
|  |  |  | 3' | G | G | C | G | G | C | G | G | C | 5' |  |
| 46 | 5' | T | T | *U | *U | A | *U | *U | A | *U | *U | A | T T 3' |  |
|  |  |  |  | A | A | *U | A | A | *U | A | A | *U |  | 31.2 |
| 47 | 5' | T | T | 4Me[C] | 4Me[C] | G | 4Me[C] | 4Me[C] | G | 4Me[C] | 4Me[C] | G | T T 3' |  |
|  |  |  |  | G | G | 4Me[C] | G | G | 4Me[C] | G | G | 4Me[C] |  | 33.3 |
| 48 | 5' | T | T | *U | *U | A | *U | *U | A | *U | *U | A | T T 3' |  |
|  |  |  |  | A | A | T | A | A | T | A | A | T |  | 26.1 |
| 49 | 5' | T | T | *U | *U | A | *U | *U | A | *U | *U | A | T T 3' |  |
|  |  |  |  | A | A | T | c | A | T | A | A | T |  | 8.1 |
| 50 | 5' | T | T | *U | *U | A | *U | *U | A | *U | *U | A | T T 3' |  |
|  |  |  |  | A | A | T | g | A | T | A | A | T |  | 8.4 |
| 51 | 5' | T | T | *U | *U | A | *U | *U | A | *U | *U | A | T T 3' |  |
|  |  |  |  | A | A | T | t | A | T | A | A | T |  | 7.8 |

\* 5Propynyle
U : U

FIG. 9

| Duplex | Sequence | *Tm(°C) |
|---|---|---|
| 52 | 5' T T [T C G T T G T C G] T T 3'<br>    T [A G C A A C A G C] 3' 5' | 46 |
| 2 | 5' T T [T C G T C G T C G] T T 3'<br>    T [A G C A G C A G C] 3' 5' | 51.3 |
| 53 | 5' T T [T C G T C(7C) G T C G] T T 3'<br>    [A G C A G C A G C] | 50.1 |
| 54 | 5' T T [T C G T C G T C G] T T 3'<br>    T [A G C A I C A G C] 3' 5' | 44.6 |
| 55 | 5' T T [T C G T C(2Me) G T C G] T T 3'<br>    [A G C A G C A G C] | 53.2 |
| 56 | 5' T T [T C G T C(2Et) G T C G] T T 3'<br>    [A G C A G C A G C] | 50.4 |
| 57 | 5' T T [T C G T C(2Pro) G T C G] T T 3'<br>    [A G C A G C A G C] | 51 |
| 58 | 5' T T [T C G T C(2iPro) G T C G] T T 3'<br>    [A G C A G C A G C] | 48.1 |
| 59 | 5' T T [T C G T C(2iButyryl) G T C G] T T 3'<br>    [A G C A G C A G C] | 41.3 |
| 60 | 5' T T [T C G T C(8Br) G T C G] T T 3'<br>    [A G C A G C A G C] | 40.3 |
| 60 | 5' T T [T C G T C(8Br) G T C G] T T 3'<br>    [A G C A G C A G C] | 40.3 |

FIG. 10

| Duplex | | | | | | | | | | | | | | *Tm(°C) |
|---|---|---|---|---|---|---|---|---|---|---|---|---|---|---|
| 2 | 5' T | T | T | C | G | T | C | G | T | C | G | T | T 3' | 51.3 |
|   |      | 3' | A | G | C | A | G | C | A | G | C | 5' |      |      |

| | | | | | | | | | | | | | Tm |
|---|---|---|---|---|---|---|---|---|---|---|---|---|---|
| 5' T | T | T | C | G | T | a | G | T | C | G | T | T 3' | 34.5 |
|      | 3' | A | G | C | A | G | C | A | G | C | 5' |      |      |

7C
A  G  C  A  G  C  A  G  C    35.5

3'  A  G  C  A  I  C  A  G  C  5'  39.5

2Et
A  G  C  A  G  C  A  G  C    33.2

2Pro
A  G  C  A  G  C  A  G  C    33.9

2iPro
A  G  C  A  G  C  A  G  C    30.7

2iButyryl
A  G  C  A  G  C  A  G  C    33.1

| Duplex | | | | | | | | | | | | | *Tm(°C) |
|---|---|---|---|---|---|---|---|---|---|---|---|---|---|
| 2 | 5' | T | T | T C G T : C : G T C G | T | T | 3' | | | | | | 51.3 |
|   |   |   |   | A G C A : G : C A G C | 5' | | | | | | | | |
| | 5' | T | T | T C G T : t : G T C G | T | T | 3' | | | | | | 37.7 |
| | | | 3' | A G C A : G : C A G C | 5' | | | | | | | | |
| | | | | | 7C | | | | | | | | |
| | | | | A G C A [G] C A G C | | | | | | | | | 39.8 |
| | | | 3' | A G C A [I] C A G C 5' | | | | | | | | | 37.6 |
| | | | | | 2Et | | | | | | | | |
| | | | | A G C A [G] C A G C | | | | | | | | | 38.6 |
| | | | | | 2Pro | | | | | | | | |
| | | | | A G C A [G] C A G C | | | | | | | | | 40.4 |
| | | | | | 2iPro | | | | | | | | |
| | | | | A G C A [G] C A G C | | | | | | | | | 37.1 |
| | | | | | 2iButyryl | | | | | | | | |
| | | | | A G C A [G] C A G C | | | | | | | | | 32.8 |
| | | | | | 8Br | | | | | | | | |
| | | | | A G C A [G] C A G C | | | | | | | | | 27 |

FIG. 12

| Duplex | | | | | | | | | | | | | *Tm(°C) |
|---|---|---|---|---|---|---|---|---|---|---|---|---|---|
| 2 | 5' T T | T | C | G | T | C | G | T | C | G | T T 3' | | |
| | 3' | A | G | C | A | G | C | A | G | C | 5' | | 51.3 |
| | | | | | | | | | | | | | |
| | 5' T T | T | C | G | T | g | G | T | C | G | T T 3' | | |
| | 3' | A | G | C | A | G | C | A | G | C | 5' | | 32.8 |

|  |  |  |  | 7C |  |  |  |  |  |
|---|---|---|---|---|---|---|---|---|---|
| A | G | C | A | G | C | A | G | C | 29.8 |

| 3' | A | G | C | A | I | C | A | G | C | 5' | 31.6 |

|  |  |  |  | 2Et |  |  |  |  |  |
|---|---|---|---|---|---|---|---|---|---|
| A | G | C | A | G | C | A | G | C | 32.1 |

|  |  |  |  | 2Pro |  |  |  |  |  |
|---|---|---|---|---|---|---|---|---|---|
| A | G | C | A | G | C | A | G | C | 32.8 |

|  |  |  |  | 2iPro |  |  |  |  |  |
|---|---|---|---|---|---|---|---|---|---|
| A | G | C | A | G | C | A | G | C | 30.4 |

|  |  |  |  | 2iButyryl |  |  |  |  |  |
|---|---|---|---|---|---|---|---|---|---|
| A | G | C | A | G | C | A | G | C | 32.8 |

FIG. 13

| Duplex | Sequence | 1M NaCl *Tm(°C) | 4.4M TMACl **Tm(°C) | 3.5M TMACl **Tm(°C) | 3M TMACl **Tm(°C) | 2M TMACl **Tm(°C) |
|---|---|---|---|---|---|---|
| 41 | 5' T T T A T T A T T A T 3' / 3' A A T A A T A A T T A 5' | 18.7 | 36.9 | 34.3 | 32.7 | 29 |
| 45 | 5' T T C C C G C C G C T 3' / 3' A A G G G C G G C G A 5' | 63.4 | 48.3 | 51.8 | 53.8 | 56 |
| 46 | 5' T T *U *U A *U *U A *U A T 3' / 3' A A *U A A A *U A A *U T 5' | 31.2 | 57.4 | 50.9 | 47.5 | 41.7 |
| 48 | 5' T T *U *U A *U *U A *U A T 3' / 3' A A T A A T A A T T 5' | 26.1 |  | 42.6 |  |  |
| 49 | 5' T T *U *U A *U *U A *U A T 3' / 3' A A T c A T A A T T 5' | 8.1 |  | 18.8 |  |  |
| 50 | 5' T T *U *U A *U *U A *U A T 3' / 3' A A T g A T A A T T 5' | 8.4 |  | 25.7 |  |  |
| 51 | 5' T T *U A *U *U A *U *U A T 3' / 3' A A T t A T A A T T 5' | 7.8 |  | 25.7 |  |  |

*U  5Propynyle U

SEQUENCE LISTING

```
<160> NUMBER OF SEQ ID NOS: 57

<210> SEQ ID NO 1
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-methyl-2'-deoxycytidine

<400> SEQUENCE: 1 cgangacga                                                           9

<210> SEQ ID NO 2
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-ethyl-2'-deoxycytidine

<400> SEQUENCE: 2 cgangacga                                                           9

<210> SEQ ID NO 3
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-propyl-2'-deoxycytidine

<400> SEQUENCE: 3 cgangacga                                                           9

<210> SEQ ID NO 4
<211> LENGTH: 9
```

```
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-allyl-2'-deoxycytidine

<400> SEQUENCE: 4 cgangacga                                                                  9

<210> SEQ ID NO 5
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-propargyl-2'-deoxycytidine

<400> SEQUENCE: 5 cgangacga                                                                  9

<210> SEQ ID NO 6
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=1-B-D-arabinofuranosyl-cytosine

<400> SEQUENCE: 6 cgangacga                                                                  9

<210> SEQ ID NO 7
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-methyl-2'-deoxycytidine
<220> FEATURE:
<221> NAME/KEY: misc_feature
<222> LOCATION: (7)..(7)
<223> OTHER INFORMATION: n=N-4-methyl-2'-deoxycytidine

<400> SEQUENCE: 7
```

-continued cganganga                                                                9

<210> SEQ ID NO 8
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-ethyl-2'-deoxycytidine
<220> FEATURE:
<221> NAME/KEY: misc_feature
<222> LOCATION: (7)..(7)
<223> OTHER INFORMATION: n=N-4-ethyl-2'-deoxycytidine

<400> SEQUENCE: 8 cganganga                                                                9

<210> SEQ ID NO 9
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-propyl-2'-deoxycytidine
<220> FEATURE:
<221> NAME/KEY: misc_feature
<222> LOCATION: (7)..(7)
<223> OTHER INFORMATION: n=N-4-propyl-2'-deoxycytidine

<400> SEQUENCE: 9 cganganga                                                                9

<210> SEQ ID NO 10
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=1-B-D-arabinofuranosyl-cytosine
<220> FEATURE:
<221> NAME/KEY: misc_feature
<222> LOCATION: (7)..(7)
<223> OTHER INFORMATION: n=1-B-D-arabinofuranosyl-cytosine

<400> SEQUENCE: 10 cganganga                                                                9

<210> SEQ ID NO 11
<211> LENGTH: 9
<212> TYPE: DNA
<213> ORGANISM: Artificial Sequence

```
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (2)..(2)
<223> OTHER INFORMATION: n=N-4-ethyl-2'-deoxycytidine
<220> FEATURE:
<221> NAME/KEY: misc_feature
<222> LOCATION: (5)..(5)
<223> OTHER INFORMATION: n=N-4-ethyl-2'-deoxycytidine
<220> FEATURE:
<221> NAME/KEY: misc_feature
<222> LOCATION: (8)..(8)
<223> OTHER INFORMATION: n=N-4-ethyl-2'-deoxycytidine

<400> SEQUENCE: 11 anaanaana                                                            9

<210> SEQ ID NO 12
<211> LENGTH: 13
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(13)
<223> OTHER INFORMATION: Artificial Sequence
<220> FEATURE:
<221> NAME/KEY: misc_feature
<222> LOCATION: (4)..(4)
<223> OTHER INFORMATION: n=N-4-methyl-2'-deoxycytidine
<220> FEATURE:
<221> NAME/KEY: misc_feature
<222> LOCATION: (7)..(7)
<223> OTHER INFORMATION: n=N-4-methyl-2'-deoxycytidine
<220> FEATURE:
<221> NAME/KEY: misc_feature
<222> LOCATION: (10)..(10)
<223> OTHER INFORMATION: n=N-4-methyl-2'-deoxycytidine

<400> SEQUENCE: 12
tttngtngtn gtt                                                      13

<210> SEQ ID NO 13
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (1)..(1)
<223> OTHER INFORMATION: n=N-4-methyl-2'-deoxycytidine
<220> FEATURE:
<221> NAME/KEY: misc_feature
<222> LOCATION: (4)..(4)
<223> OTHER INFORMATION: n=N-4-methyl-2'-deoxycytidine
<220> FEATURE:
<221> NAME/KEY: misc_feature
<222> LOCATION: (7)..(7)
<223> OTHER INFORMATION: n=N-4-methyl-2'-deoxycytidine

<400> SEQUENCE: 13 nganganga                                                            9
```

```
<210> SEQ ID NO 14
<211> LENGTH: 13
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(13)
<223> OTHER INFORMATION: Artificial Sequence
<220> FEATURE:
<221> NAME/KEY: misc_feature
<222> LOCATION: (4)..(4)
<223> OTHER INFORMATION: n=N-4-ethyl-2'-deoxycytidine
<220> FEATURE:
<221> NAME/KEY: misc_feature
<222> LOCATION: (7)..(7)
<223> OTHER INFORMATION: n=N-4-ethyl-2'-deoxycytidine
<220> FEATURE:
<221> NAME/KEY: misc_feature
<222> LOCATION: (10)..(10)
<223> OTHER INFORMATION: n=N-4-ethyl-2'-deoxycytidine

<400> SEQUENCE: 14
tttngtngtn gtt                                                     13

<210> SEQ ID NO 15
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (1)..(1)
<223> OTHER INFORMATION: n=N-4-ethyl-2'-deoxycytidine
<220> FEATURE:
<221> NAME/KEY: misc_feature
<222> LOCATION: (4)..(4)
<223> OTHER INFORMATION: n=N-4-ethyl-2'-deoxycytidine
<220> FEATURE:
<221> NAME/KEY: misc_feature
<222> LOCATION: (7)..(7)
<223> OTHER INFORMATION: n=N-4-ethyl-2'-deoxycytidine

<400> SEQUENCE: 15 nganganga                                                           9

<210> SEQ ID NO 16
<211> LENGTH: 13
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(13)
<223> OTHER INFORMATION: Artificial Sequence
<220> FEATURE:
<221> NAME/KEY: misc_feature
<222> LOCATION: (4)..(4)
<223> OTHER INFORMATION: n=N-4-ethyl-2'-deoxycytidine
<220> FEATURE:
<221> NAME/KEY: misc_feature
<222> LOCATION: (7)..(7)
<223> OTHER INFORMATION: n=N-4-ethyl-2'-deoxycytidine
<220> FEATURE:
<221> NAME/KEY: misc_feature
<222> LOCATION: (10)..(10)
<223> OTHER INFORMATION: n=N-4-ethyl-2'-deoxycytidine
```

```
<400> SEQUENCE: 16
tttngtnttn gtt                                                      13

<210> SEQ ID NO 17
<211> LENGTH: 13
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(13)
<223> OTHER INFORMATION: Artificial Sequence
<220> FEATURE:
<221> NAME/KEY: misc_feature
<222> LOCATION: (3)..(4)
<223> OTHER INFORMATION: n=5-propynyldeoxyuridine
<220> FEATURE:
<221> NAME/KEY: misc_feature
<222> LOCATION: (6)..(7)
<223> OTHER INFORMATION: n=5-propynyldeoxyuridine
<220> FEATURE:
<221> NAME/KEY: misc_feature
<222> LOCATION: (9)..(10)
<223> OTHER INFORMATION: n=5-propynyldeoxyuridine

<400> SEQUENCE: 17
ttnnannann att                                                      13

<210> SEQ ID NO 18
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (1)..(1)
<223> OTHER INFORMATION: n=5-propynyldeoxyuridine
<220> FEATURE:
<221> NAME/KEY: misc_feature
<222> LOCATION: (4)..(4)
<223> OTHER INFORMATION: n=5-propynyldeoxyuridine
<220> FEATURE:
<221> NAME/KEY: misc_feature
<222> LOCATION: (7)..(7)
<223> OTHER INFORMATION: n=5-propynyldeoxyuridine

<400> SEQUENCE: 18 naanaanaa                                                            9

<210> SEQ ID NO 19
<211> LENGTH: 13
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(13)
<223> OTHER INFORMATION: Artificial Sequence
<220> FEATURE:
<221> NAME/KEY: misc_feature
<222> LOCATION: (3)..(4)
<223> OTHER INFORMATION: n=N-2'-methyl-2'-deoxycytidine
<220> FEATURE:
<221> NAME/KEY: misc_feature
<222> LOCATION: (6)..(7)
```

```
<223> OTHER INFORMATION: n=N-2'-methyl-2'-deoxycytidine
<220> FEATURE:
<221> NAME/KEY: misc_feature
<222> LOCATION: (9)..(10)
<223> OTHER INFORMATION: n=N-2'-methyl-2'-deoxycytidine

<400> SEQUENCE: 19
ttnnannann att                                                          13

<210> SEQ ID NO 20
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (1)..(1)
<223> OTHER INFORMATION: n=N-4'-methyl-2'-deoxycytidine
<220> FEATURE:
<221> NAME/KEY: misc_feature
<222> LOCATION: (4)..(4)
<223> OTHER INFORMATION: n=N-4'-methyl-2'-deoxycytidine
<220> FEATURE:
<221> NAME/KEY: misc_feature
<222> LOCATION: (7)..(7)
<223> OTHER INFORMATION: n=N-4'-methyl-2'-deoxycytidine

<400> SEQUENCE: 20 nggnggngg                                                                9

<210> SEQ ID NO 21
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=7-deazadeoxyguanosine

<400> SEQUENCE: 21 cgacnacga                                                                9

<210> SEQ ID NO 22
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=i

<400> SEQUENCE: 22 cgacnacga                                                                9
```

```
<210> SEQ ID NO 23
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=N-2-ethyldeoxyguanosine

<400> SEQUENCE: 23 cgacnacga                                                                  9

<210> SEQ ID NO 24
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=N-2-propyldeoxyguanosine

<400> SEQUENCE: 24 cgacnacga                                                                  9

<210> SEQ ID NO 25
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=N-2-isopropyldeoxyguanosine

<400> SEQUENCE: 25 cgacnacga                                                                  9

<210> SEQ ID NO 26
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=2-iso-Butyrylguanosine

<400> SEQUENCE: 26 cgacnacga                                                                  9
```

```
<210> SEQ ID NO 27
<211> LENGTH: 9
<212> TYPE: DNA
<213> ORGANISM: Artificial Sequence
<220> FEATURE:
<223> OTHER INFORMATION: a nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=modified deoxycytidine

<400> SEQUENCE: 27 cgangacga                                                              9

<210> SEQ ID NO 28
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artifical Sequence

<400> SEQUENCE: 28
tttcgtcatc gtt                                                        13

<210> SEQ ID NO 29
<211> LENGTH: 13
<212> TYPE: DNA
<213> ORGANISM: Artificial Sequence
<220> FEATURE:
<223> OTHER INFORMATION: Artificial
<220> FEATURE:
<221> NAME/KEY: misc_feature
<222> LOCATION: (1)..(13)
<223> OTHER INFORMATION: Artificial Sequence

<400> SEQUENCE: 29
tttcgtcctc gtt                                                        13

<210> SEQ ID NO 30
<211> LENGTH: 13
<212> TYPE: DNA
<213> ORGANISM: Artificial Sequence
<220> FEATURE:
<223> OTHER INFORMATION: Artificial
<220> FEATURE:
<221> NAME/KEY: misc_feature
<222> LOCATION: (1)..(13)
<223> OTHER INFORMATION: Artificial Sequence

<400> SEQUENCE: 30
tttcgtcttc gtt                                                        13

<210> SEQ ID NO 31
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence
```

-continued

```
<400> SEQUENCE: 31 cgatgacga                                                                 9

<210> SEQ ID NO 32
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 32
tttcgtcgtc gtt                                                           13

<210> SEQ ID NO 33
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 33 cgacgacga                                                                 9

<210> SEQ ID NO 34
<211> LENGTH: 9
<212> TYPE: DNA
<213> ORGANISM: Artificial Sequence
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (4)..(4)
<223> OTHER INFORMATION: n=N-4-propyl-2'-deoxycytidine

<400> SEQUENCE: 34 cgangatga                                                                 9

<210> SEQ ID NO 35
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 35
tttcatcatc gtt                                                           13

<210> SEQ ID NO 36
<211> LENGTH: 9
<212> TYPE: DNA
<213> ORGANISM: Artificial Sequence
<220> FEATURE:
```

```
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 36 cgatgatga                                                                        9

<210> SEQ ID NO 37
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 37
tttattatta ttt                                                                  13

<210> SEQ ID NO 38
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 38 ataataata                                                                        9

<210> SEQ ID NO 39
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 39
tttgttgttg ttt                                                                  13

<210> SEQ ID NO 40
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 40 acaacaaca                                                                        9

<210> SEQ ID NO 41
<211> LENGTH: 13
<212> TYPE: DNA
<213> ORGANISM: Artificial Sequence
```

```
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 41
tttgttgttg ttt                                                              13

<210> SEQ ID NO 42
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 42
tttcgttgtc gtt                                                              13

<210> SEQ ID NO 43
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 43
tttcgtagtc gtt                                                              13

<210> SEQ ID NO 44
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 44
ttttattatt att                                                              13

<210> SEQ ID NO 45
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 45 taataataa                                                                    9

<210> SEQ ID NO 46
<211> LENGTH: 13
<212> TYPE: DNA
```

```
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 46
ttccgccgcc gtt                                                        13

<210> SEQ ID NO 47
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 47 cggcggcgg                                                              9

<210> SEQ ID NO 48
<211> LENGTH: 9
<212> TYPE: DNA
<213> ORGANISM: Artificial Sequence
<220> FEATURE:
<223> OTHER INFORMATION: nucleotide with modified bases
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (1)..(1)
<223> OTHER INFORMATION: n=5-propynyldeoxyuridine
<220> FEATURE:
<221> NAME/KEY: misc_feature
<222> LOCATION: (4)..(4)
<223> OTHER INFORMATION: n=5-propynyldeoxyuridine
<220> FEATURE:
<221> NAME/KEY: misc_feature
<222> LOCATION: (7)..(7)
<223> OTHER INFORMATION: n=5-propynyldeoxyuridine

<400> SEQUENCE: 48 naanaanaa                                                              9

<210> SEQ ID NO 49
<211> LENGTH: 13
<212> TYPE: DNA
<213> ORGANISM: Artificial Sequence
<220> FEATURE:
<223> OTHER INFORMATION: Nucleotide with modified bases
<220> FEATURE:
<221> NAME/KEY: misc_feature
<222> LOCATION: (1)..(13)
<223> OTHER INFORMATION: Artificial Sequence
<220> FEATURE:
<221> NAME/KEY: misc_feature
<222> LOCATION: (3)..(4)
<223> OTHER INFORMATION: n=N-4-methyl-2'deoxycytidine
<220> FEATURE:
<221> NAME/KEY: misc_feature
<222> LOCATION: (6)..(7)
<223> OTHER INFORMATION: n=N-4-methyl-2'deoxycytidine
<220> FEATURE:
<221> NAME/KEY: misc_feature
<222> LOCATION: (9)..(10)
<223> OTHER INFORMATION: n=N-4-methyl-2'deoxycytidine
```

```
<400> SEQUENCE: 49
ttnngnngnn gtt                                                          13

<210> SEQ ID NO 50
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 50 taatactaa                                                                9

<210> SEQ ID NO 51
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 51 taatagtaa                                                                9

<210> SEQ ID NO 52
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 52 taatattaa                                                                9

<210> SEQ ID NO 53
<211> LENGTH: 9
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(9)
<223> OTHER INFORMATION: Artificial Sequence

<400> SEQUENCE: 53 cgacaacga                                                                9

<210> SEQ ID NO 54
<211> LENGTH: 9
<212> TYPE: DNA
<213> ORGANISM: Artificial Sequence
```

-continued

```
<220> FEATURE:
<223> OTHER INFORMATION: nucleotide with a modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=N-2-methyldeoxyguanosine

<400> SEQUENCE: 54 cgacnacga                                                                  9

<210> SEQ ID NO 55
<211> LENGTH: 9
<212> TYPE: DNA
<213> ORGANISM: Artificial Sequence
<220> FEATURE:
<223> OTHER INFORMATION: nucleotide with a  modified base
<220> FEATURE:
<221> NAME/KEY: misc_feature
<222> LOCATION: (1)..(9)
<223> OTHER INFORMATION: Artificial Sequence
<220> FEATURE:
<221> NAME/KEY: misc_feature
<222> LOCATION: (5)..(5)
<223> OTHER INFORMATION: n=8-bromo-deoxyguanosine

<400> SEQUENCE: 55 cgacnacga                                                                  9

<210> SEQ ID NO 56
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 56
tttcgtagtc gtt                                                            13

<210> SEQ ID NO 57
<211> LENGTH: 13
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(13)
<223> OTHER INFORMATION: Artificial Sequence

<400> SEQUENCE: 57
tttcgtggtc gtt                                                            13
```

METHOD FOR PRODUCING HYBRIDIZATION COMPLEXES WHOSE STABILITY IS SUBSTANTIALLY INDEPENDENT OF THE BASE COMPOSITION OF TWO HYBRIDIZED NUCLEIC ACID MOLECULES

BACKGROUND OF THE INVENTION

The present invention relates to a method for producing hybridisation complexes whose stability is substantially independent of the base composition of two hybridised nucleic acid molecules. The invention also relates to the use of this method for the assay of nucleic acid sequences. The invention further relates to hybridisation complexes produced from two complementary, or substantially complementary, nucleic acid molecules whose stability is substantially independent of the base composition of said two hybridised nucleic acid molecules.

The pairing law A-T (or A-U) and G-C gives nucleic acids the property of forming specific hybridisation complexes between complementary sequences. This long known hybridisation property means that a fragment of nucleic acid, or an oligonucleotide, can be used as a probe to display the presence of a complementary nucleic sequence. The analysis of DNA fragments after gel separation (E. Southern, J. Mol. Biol., 1975, 98, 503–517) is today widely used both in the area of fundamental research and in medical analysis (Caskey, Science, 1987, 236, 1223–1228; Landegrer et al., Science, 1988, 242, 229–237; Arnheim et al., Ann rev. Biochem., 1992, 61, 131–156).

Several assay techniques of nucleic acids based on their hybridisation property with probes have been developed, in particular for the sequencing of unknown DNAs or RNAs, the detection of sequences associated with a pathology, and the search for point mutations in sequences (S. Ikata et al., Nuclei Acids Res., 1987, 15, 797–811; J. A. Matthews, L. J. Krieka, Analytical Biochemistry, 1988, 169, 1–25).

More recently, new assay and sequencing methods for unknown DNA fragments have been put forward, based on hybridisation with a series of oligonucleotides immobilised on a solid support (E. Southern, European Patent published under number: 0 373 203; K. R. Khrapko et al., FEBS Letters, 1989, 256, 118–122; R. Drmanac et al., Genomics, 1989, 4, 114–128; R. Drmanac et al., DNA and Cell Biology, 1990, 9, 527–534; K. R. Khrapko et al., J. DNA Sequencing Mapp., 1991, 1, 375–388; R. Drmanac et al., Science 1993, 260, 1649–1652; R. J. Lipshutz, J. Biomol. Struct. Dyn., 1993, 11, 637–653; U. Maskos, E. Southern, Nucleic Acids Res., 1993, 21, 4663–4669; A. C. Pease et al., Proc. Natl. Acad. Sci., USA, 1994, 91, 5022–5026; J. C. Williams, Nucleic Acids Res., 1994, 22, 1365–1367; E. M. Southern, Nucleic Acids Res., 1994, 22, 1368–1373. These new methods consist of detecting the signals emitted by hybrids produced by pairing a labelled DNA with a series of oligonucleotides having the same length and different sequences immobilised on a membrane or glass surface, then of reconstructing the sequence of the DNA fragment using an algorithmic process. The assay of the hybridisation complexes obtained with the above methods is based on the greater stability of the hybrids without mismatch in relation to that of hybrids containing one or more mismatches. The distinction between a perfect hybrid and a hybrid with mismatch may be made for example by raising the temperature of the medium, which produces dissociation of the complexes with mismatch before dissociation of the complexes without mismatch.

However, the use of natural oligonucleotides in the preceding techniques which also use a great number of these probe oligonucleotides, comes up against a fundamental difficulty connected with the difference in hybrid stability in relation to the base composition of the immobilised oligonucleotides. Indeed, it is known that the base pair G-C, characterized by three hydrogen bonds, is more stable than the pairs A-T or A-U which only have two hydrogen bonds. Therefore, the stability of perfect hybrids produced by sequences with a high number of A-T pairs, is likely to be close to or even less than the stability of imperfect hybrids comprising a mismatch and produced by sequences having the same length but with a high number of G-C pairs. This phenomenon leads to false-positive or false-negative signals depending upon hybridisation temperature and wash conditions.

The use of oligonucleotides formed by the natural nucleosides dA, dG, dC, T or dU, therefore raises a major obstacle against the development of these new techniques for the assay of nucleic acid sequences. The risk of failure in distinguishing between perfect and imperfect hybrids also implies systematic control of a great number of oligonucleotides under determined temperature and medium conditions.

To remedy this drawback, the prior art proposed a hybridisation method using tetramethylammonium chloride to reduce differences in hybrid stability related to base composition (W. B. Melchior, P. H. von Hippel, Proc. Natl. Acad. Sci., USA, 1973, 70, 298–302; U. Maskos, E. M. Southern, Nucleic Acids Res., 1993, 21, 4663–4669), but the results obtained were contradicted by other nucleotide sequences (P. V. Riccelli, A. S. Beright, Nucleic Acids Res., 1993, 21, 3785–3788).

The suggestion was also put forward of varying the density of the oligonucleotides immobilised on polyacrylamide gel in relation to their base composition (K. R. Khrapko et al., J. DNA Sequencing Mapp., 1991, 1, 375–388). But this strategy considerably complicates the system when it is applied with a great number of immobilised oligonucleotides. The use has also been contemplated of modified bases such as 5-CldU and 2-$NH_2$dA, however substantial variation in hybrid stability was observed (J. D. Heisel, H. Lehrach, FEBS Lett., 1990, 274, 103–106). Also, European patent application EP-A-0 176 396 describes a method for producing a complex between a nucleotide probe and a nucleic acid in which at least one part of the adenine groups of the probe is replaced by groups of modified adenine. The modified adenine groups are likely to form three hydrogen bonds and therefore increase the stability of the complex produced. The gain in stability obtained with such probes enables hybridisation to be produced despite the presence of mismatches.

It was also suggested, in international patent N° WO-A-305 175, to make use of nucleotides comprising analogues of pyrimidic bases in PCR or hybridisation reactions.

The bases used in the methods described in D2 form pairs whose stability is close both to A and to G.

Another approach using oligomers constructed with deoxyribonucleosides and ribonucleosides to destabilise the hybrids of sequences with a high number of G and C bases has also been described (Jörg D. Hoheisel, Nucleic Acids Research, 1996, vol. 24. No. 3), but the quantity of hybrids produced with these oligonucleotides falls very rapidly when the alternation number increases. Also, heat dissociation of these hybrids extends over a very wide temperature zone, which means that differentiating between perfect hybrids and hybrids with mismatch becomes largely unreliable.

SUMMARY OF THE INVENTION

The present invention therefore sets out to provide a method with which hybridisation complexes can be produced whose stability is substantially independent of the base composition of the two hybridised nucleic acid molecules. This purpose is achieved with a method consisting of contacting a first nucleic acid molecule with a second nucleic acid molecule under conditions enabling the formation of a specific hybridisation complex, characterized in that at least one of the four types of bases contained in the sequence of the first and/or second nucleic acid molecule is a modified base having pairing properties close to those of the natural base it replaces, such that at least one of the two types of base pair contained in the composition of the complex comprises a modified base, and in that the totality of the base pairs contained in the composition of the said complex is of like stability.

BRIEF DESCRIPTION OF FIGURES

FIG. 1 shows the Tm values of the double strands formed by natural tridecadeoxynucleotides with natural nonadeoxynucleotides and with nonadeoxynucleotides comprising a modified deoxycytidine dC*. Duplex 1 is formed from SEQ ID NOs: 28 and 31. Duplex 2 is formed from SEQ ID NOs: 32 and 33. Duplex 3 is formed from SEQ ID NOs: 32 and 1. Duplex 4 is formed from SEQ ID NOs: 32 and 2. Duplex 5 is formed from SEQ ID NOs: 32 and 34. Duplex 6 is formed from SEQ ID NOs: 32 and 4. Duplex 7 is formed from SEQ ID NOs: 32 and 5. Duplex 8 is formed from SEQ ID NOs: 32 and 6.

FIG. 3 shows that destabilisation due to the mismatches of A-C* (duplex 15 to 20) is equivalent to that of the mismatch of A-C (duplex 14). Duplex 14 is formed from SEQ ID NOs: 28 and 33. Duplex 15 is formed from SEQ ID NOs: 28 and 1. Duplex 16 is formed from SEQ ID NOs: 28 and 2. Duplex 17 is formed from SEQ ID NOs: 28 and 3. Duplex 18 is formed from SEQ ID NOs: 28 and 4. Duplex 19 is formed from SEQ ID NOs: 28 and 5. Duplex 20 is formed from SEQ ID NOs: 28 and 6.

FIG. 4 shows that destabilisation due to the mismatches of C-C* (duplex 22 to 27) is equivalent to that of the mismatch of C-C (duplex 21). Duplex 21 is formed from SEQ ID NOs: 29 and 33. Duplex 22 is formed from SEQs ID NOs: 29 and 1. Duplex 23 is formed from SEQ ID NOs: 29 and 2. Duplex 24 is formed from SEQ ID NOs: 29 and 3. Duplex 25 is formed from SEQ ID NOs: 29 and 4. Duplex 26 is formed from SEQ ID NOs: 29 and 5. Duplex 27 is formed from SEQ ID NOs: 29 and 6.

FIG. 5 shows that destabilisation due to the mismatches of T-C* (duplex 29 to 34) is equivalent to that of mismatches T-C (duplex 28). Duplex 28 is formed from SEQ ID NOs: 30 and 33. Duplex 29 is formed from SEQs ID NOs: 30 and 1. Duplex 30 is formed from SEQ ID NOs: 30 and 2. Duplex 31 is formed from SEQ ID NOs: 30 and 3. Duplex 32 is formed from SEQ ID NOs: 30 and 4. Duplex 33 is formed from SEQ ID NOs: 30 and 5. Duplex 34 is formed from SEQ ID NOs: 30 and 6.

FIG. 6 shows that the replacement of 3 A-T pairs of duplex 35 by three G-$C^{4Et}$ pairs leads to duplex 37 with much the same Tm. Duplex 35 is formed from SEQ ID NOs: 37 and 38. Duplex 36 is formed from SEQs ID NOs: 39 and 40. Duplex 37 is formed from SEQ ID NOs: 41 and 11. Duplex 38 is formed from SEQ ID NOs: 42 and 11. Duplex 39 is formed from SEQ ID NOs: 32 and 11. Duplex 40 is formed from SEQ ID NOs: 43 and 11.

FIG. 7 shows that when the 6 A-T pairs of duplex 41 are replaced by 6 G-C pairs (duplex 2) the variation in Tm is very high. Duplex 28 is formed from SEQ ID NOs: 30 and 33. Duplex 21 is formed from SEQs ID NOs: 29 and 33. Duplex 14 is formed from SEQ ID NOs: 28 and 33. Duplex 2 is formed from SEQ ID NOs: 32 and 33. Duplex 41 is formed from SEQ ID NOs: 44 and 45. Duplex 42 is formed from SEQ ID NOs: 12 and 13. Duplex 43 is formed from SEQ ID NOs: 14 and 15. Duplex 44 is formed from SEQ ID NOs: 16 and 15.

FIG. 8 shows that duplex 46 which comprises 9 A-$U^{5Propynyl}$ base pairs has an equivalent Tm to that of duplex 47 comprising 9 G-$C^{N4Met}$ pairs. Duplex 41 is formed from SEQ ID NOs: 44 and 45. Duplex 45 is formed from SEQs ID NOs: 46 and 47. Duplex 46 is formed from SEQ ID NOs: 17 and 48. Duplex 47 is formed from SEQ ID NOs: 49 and 20. Duplex 48 is formed from SEQ ID NOs: 17 and 45. Duplex 49 is formed from SEQ ID NOs: 17 and 50. Duplex 50 is formed from SEQ ID NOs: 17 and 51. Duplex 51 is formed from SEQ ID NOs: 17 and 52.

FIG. 9 shows the Tm values of double strands formed between a tridecadeoxynucleotide and nonadeoxynucleotides comprising a modified deoxyguanosine dG*. Duplex 52 is formed from SEQ ID NOs: 42 and 53. Duplex 2 is formed from SEQs ID NOs: 32 and 33. Duplex 53 is formed from SEQ ID NOs: 32 and 21. Duplex 54 is formed from SEQ ID NOs: 32 and 22. Duplex 55 is formed from SEQ ID NOs: 32 and 54. Duplex 56 is formed from SEQ ID NOs: 32 and 23. Duplex 57 is formed from SEQ ID NOs: 32 and 24. Duplex 58 is formed from SEQ ID NOs: 32 and 25. Duplex 59 is formed from SEQ ID NOs: 32 and 26. Duplex 60 is formed from SEQ ID NOs: 32 and 55.

FIG. 10 shows that a mismatch A-G* leads to considerable destabilisation. Duplex 2 is formed from SEQ ID NOs: 32 and 33. The second duplex is formed from SEQs ID NOs: 56 and 33. SEQ ID NOs: 21 through 26 and 55 are listed.

FIG. 11 shows that a mismatch T-G* leads to considerable destabilisation. Duplex 2 is formed from SEQ ID NOs: 32 and 33. The second duplex is formed from SEQs ID NOs: 42 and 33. SEQ ID NOs: 21 through 26 and 55 are listed.

FIG. 12 shows that a mismatch G-G* leads to considerable destabilisation. Duplex 2 is formed from SEQ ID NOs: 32 and 33. The second duplex is formed from SEQs ID NOs: 57 and 33. SEQ ID NOs: 21 through 26 are listed.

FIG. 13 shows that for a given medium the Tm value of duplex 41 made up of 9 A-T base pairs is lower than that of duplex 45 made up of 9 G-C base pairs. Duplex 41 is formed from SEQ ID NOs: 44 and 45. Duplex 45 is formed from SEQs ID NOs: 46 and 47. Duplex 46 is formed from SEQ ID NOs: 17 and 48. Duplex 48 is formed from SEQ ID NOs: 17 and 45. Duplex 49 is formed from SEQ ID NOs: 17 and 50. Duplex 50 is formed from SEQ ID NOs: 17 and 51. Duplex 51 is formed from SEQ ID NOs: 17 and 52.

DETAILED DESCRIPTION OF THE INVENTION

Figure 2:
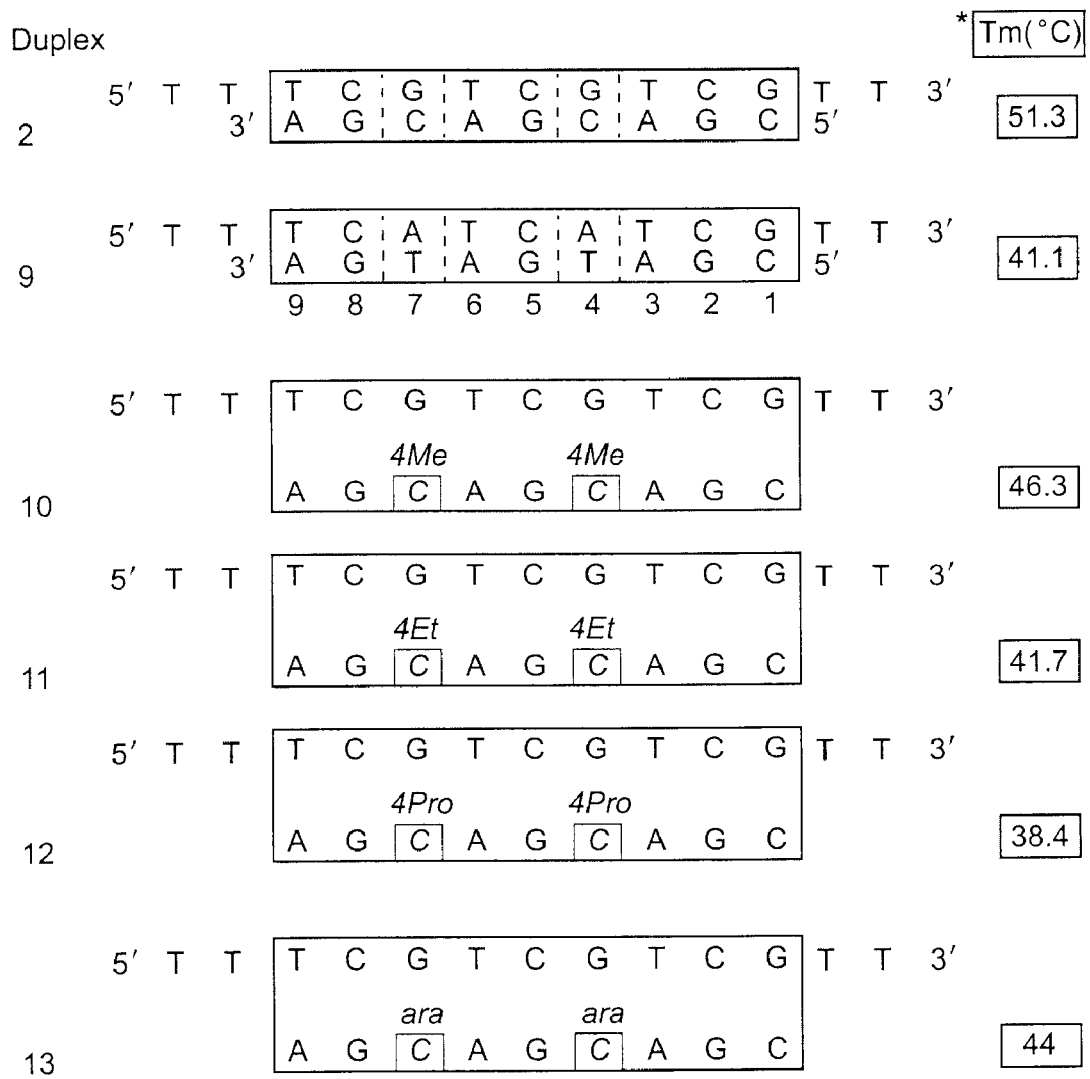
FIG. 2 shows the Tm values of the double strands formed by natural tridecadeoxynucleotides with natural nonadeoxynucleotides and with nonadeoxynucleotides comprising a modified deoxycytidine dC*. Duplex 2 is formed from SEQ ID NOs: 32 and 33. Duplex 9 is formed from SEQ ID NOs: 35 and 36. Duplex 10 is formed from SEQ ID NOs: 32 and 7. Duplex 11 is formed from SEQ ID NOs: 32 and 8. Duplex 12 is formed from SEQ ID NOs: 32 and 9. Duplex 13 is formed from SEQ ID NOs: 32 and 10.

The nomenclature which uses a letter to designate below the four types of bases contained in the composition of the deoxyribonucleic acids is as follows:

deoxycytidine will be referred to either as C or dC, followed by "*" to designate the corresponding modified base, deoxyguanosine will be referred to either as G or dG followed by "*" to designate the corresponding modified base, thymidine and deoxyuridine will be referred to respectively as T or dU followed by "*" to designate the corresponding modified base, deoxyadenosine will be referred to either as A or dA, followed by "*" to designate the corresponding modified base.

To reduce the differences in hybrid stability, due to the difference in base composition, the invention suggests replacing at least one of the natural nucleosides chosen from among deoxycytidine (dC), deoxyguanosine (dG), thymidine (T) and deoxyadenosine (dA) by modified nucleosides, having due regard to the pairing law, respectively designated dC*, dG*, dU* and dA* in order to obtain nucleic acid sequences able to produce hybridisation complexes in which:

the stability of the base pairs C*-G and/or G*-C is equivalent to that of pairs A-T, and/or the stability of base pairs A*-T and/or A-T* is greater than that of pairs A-T and close to that of natural pairs C-G, or further the stability of base pairs C*-G and/or G*-C is equivalent to that of pairs A*-T and/or A-T*; in this embodiment, the stability of pairs C*-G and/or G*-C is reduced in relation to that of natural pairs G-C, and the stability of pairs A*-T and/or A-T* is increased in relation to that of natural pairs A-T.

Therefore, the method of the invention comprises several forms of implementation, in particular the four following forms.

One first embodiment of the invention is characterized in that the same type of base contained in the sequence of the first and second nucleic acid molecule is a modified base having pairing properties close to those of the natural base it replaces. In this embodiment, at least one of the same types of base (A, G, C or T) contained in the composition of the first and second nucleic acid molecule is a modified base having pairing properties close to those of the natural base it replaces. It can therefore be considered:

that only one of the four types of base contained in the sequence of the first and second nucleic acid molecule is a modified base having pairing properties close to those of the natural base it replaces, such that only one of the two types of base pairs (A-T, G-C) contained in the composition of the complex comprises a modified base.

that two of the four types of base contained in the sequence of the first and second nucleic acid molecule are modified bases having pairing properties close to those of the natural bases they replace, such that the two types of base pairs contained in the composition of the complex comprise a modified base.

A second embodiment of the method of the invention is characterized in that at least two of the four types of base contained in only one of the first and second nucleic acid molecules are modified bases having pairing properties close to those of the natural bases they replace, such that at least one of the two types of base pairs contained in the composition of the complex comprises modified bases.

The method of the invention may advantageously be used for the assay of nucleic acid sequences, in particular for the sequencing or detection of mutation. Such method comprises producing a hybridisation complex in accordance with the previously described method, in which the first nucleic acid molecule constitutes or comprises the sequence to be assayed, and the second nucleic acid molecule is a nucleic probe that can be used for sequencing or detecting point mutation, and then of assaying the hybridisation complex by any appropriate means.

One method of the invention for the assay of nucleic acids uses at least 2 bases in 1 strand that are placed in contact with the nucleic acids to be assayed, optionally labelled beforehand, with an adequate quantity of at least one nucleic probe, and then uses any appropriate means to assay the hybridisation complexes which may be produced, in particular in order to identify the presence of a mismatch.

Among the assay methods which come within the scope of this invention, particular mention may be made of detection methods by luminescence, fluorescence, colorimetry and radioactivity.

Advantageously, said nucleic probe is an oligonucleotide comprising 4 to 30 nucleosides.

One first form of embodiment of the method of the invention for the assay of nucleic acid sequences comprises:

preparing the first nucleic acid molecule using a chemical or biological method to copy all or part of the sequence to be assayed, said method using a modified nucleoside such that one of the four types of bases contained in the composition of said sequence is replaced by a modified base having pairing properties close to those of the natural base it replaces, placing in contact said first nucleic acid molecule with the second nucleic acid molecule which is a nucleic probe appropriate for sequencing or detecting point mutation, such that a hybridisation complex is produced in which one of the four types of base contained in the sequence of the first and second nucleic acid molecule is a modified base having pairing properties close to those of the natural base it replaces, such that one of the two types of base pairs contained in the composition of the complex comprises a modified base.

assaying the hybridisation complex by any appropriate means.

A second embodiment of the method of the invention for the assay of nucleic acid sequences comprises:

preparing the first nucleic acid molecule using a chemical or biological method to copy all or part of the sequence to be assayed, said method using two modified nucleosides such that two of the four types of bases contained in the composition of said sequence are replaced by two modified bases having pairing properties close to those of the natural bases they replace, placing in contact said first nucleic acid molecule with the second nucleic acid molecule which is a nucleic probe appropriate for sequencing or detecting point mutation, such that a hybridisation complex is produced in which two of the four types of bases contained in the sequence of the first and second nucleic acid molecule are modified bases having pairing properties close to those of the natural bases they replace, such that the two types of base pairs contained in the composition of the complex comprise a modified base.

assaying the hybridisation complex by any appropriate means.

One particular embodiment of the method of the invention for the assay of nucleic acid sequences is characterized in that the nucleic probe was prepared using a chemical or biological process using at least one type of modified nucleoside, such that a probe is obtained whose sequence comprises at least one modified base having pairing properties close to those of the natural base it replaces.

This embodiment particularly targets nucleic probes in which two of the four types of base contained in their composition are modified bases having pairing properties close to those of the natural bases they replace. The following combinations can therefore be considered:

nucleosides dC and dG are replaced by nucleosides dC* and dG* respectively, nucleosides dA and T are replaced by nucleosides dA* and dU* respectively, nucleosides dC and T are replaced by nucleosides dC* and dU* respectively as defined previously, in which case the first nucleic acid molecule is prepared in accordance with the second embodiment of the method for the assay of nucleic acid sequences described previously.

nucleosides dG and T are replaced by nucleosides dG* and dU* respectively in which case the first nucleic acid molecule is prepared in accordance with the second embodiment of the method of the invention for the assay of nucleic acid sequences described above, nucleosides dA and dG are replaced by nucleosides dA* and dG" respectively, in which case the first nucleic acid molecule is prepared in accordance with the second embodiment of the method of the invention for the assay of nucleic acid sequences previously described.

nucleosides dA and dC are replaced by nucleosides dA* and dC* respectively, in which case the first molecule of nucleic acid is prepared in accordance with the second embodiment of the method of the invention for the assay of nucleic acid sequences described previously.

Among the modification combinations considered above, particular preference is given to those leading to oligodeoxynucleotides in which:

All the nucleosides dC and dG are replaced by nucleosides dC* and dG* respectively. The nucleic probes made of these modified oligodeoxynucleotides can be used to produce hybridisation complexes with complementary non-modified nucleic acid sequences. This double modification of the oligodeoxynucleotides can produce hybridisation complexes in which the stability of all the base pairs G*-C and C*-G is equivalent to that of the non-modified base pairs A-T or A-U.

All the nucleosides dA and T are replaced by nucleosides dA* and dU* respectively. The nucleic probes made of these modified oligodeoxynucleotides can be used to produce hybridisation complexes with complementary non-modified nucleic acid sequences. With this double modification of the oligodeoxynucleotides it is possible to produce hybridisation complexes in which the stability of all the base pairs A*-T and A-U* is close to that of the non-modified base pairs G-C.

The other nucleic probes doubly modified at the level of only one of the nucleosides of each base pair, can be used to produce hybridisation complexes with complementary nucleic acid sequences in which the same nucleoside of each base pair is also replaced by a modified nucleoside, in order to produce hybridisation complexes whose stability is substantially independent of the base composition.

In this latter case, as in the case when only one nucleotide of one type of base pair is modified, it is necessary to submit the complementary nucleic acid to a prior modification stage to replace the same nucleoside of the base pair under consideration, such that either one of the two nucleosides of said base pair in the hybridisation complex is modified such that the stability of the hybrid is substantially independent of the base composition.

This prior modification stage of the nucleic acids is conducted whenever the oligodeoxynucleotide forming the nucleic probe only comprises:

only one of the four modified nucleosides dC*, dG*, dU* or dA*, or two of these four modified nucleosides, if the two involved do not belong to the same base pair as:

dC* and dU* or dA* dG* and dU* or dA* dU* and dC* and G* dA* and dC* and dG*.

The replacement of the natural nucleosides present in the target nucleic acids, during this prior modification stage, may be conducted by any method known to Men of the Art, such that an enzymatic polymerisation reaction is set up with one or more modified nucleosides.

According to one advantageous embodiment of the assay methods defined above, the latter are conducted using nucleic probes fixed on a support, such as membranes or cellulose threads, synthetic polymers or even glass surfaces. The oligodeoxynucleotides forming the nucleic probes may then be synthesized directly on the support.

The nucleic probes used in the preceding methods for the assay of nucleic acid sequences may also be substituted at one end at least of their 5' and/or 3' ends in particular:

by intermediate agents such as derivatives of acridine in order to increase the stability of the hybrids, by biotin to form complexes with derivatives of streptavidine, by functional groups to prepare conjugates or to immobilise them on solid supports such as for example: $-(CH_2)_n-COOH$, $-(CH_2)_n-NH_2$, $-(CH_2)_n-SH$, $-(CH_2)_n-CHOH-CH_2OH$, $-(CH_2)_nO-PO_3^2$, $-(CH_2)_n-PO_2-S$, in which n lies between 1 and 20.

These substituted oligodeoxynucleotides may be prepared in accordance with the methods described in the literature (Nguyen, T. Thuong, U. Asseline, *Oligonucleotides and analogues: A practical approach*, F. Ecksein ed., I. R. L. Press, Oxford, 1991, 283–306; U. Asseline et al., *Tetrahedron*, 1992, 48, 1233–1254).

Chemical modifications of the nucleosides dC, dG, T and dA which come within the scope of the present invention will be described below.

A first type of base which may be contained in the composition of said first and/or second nucleic acid molecule is a modified deoxycytidine which meets the following formula:

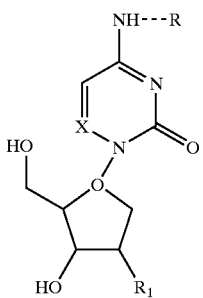

(I)

in which R represents a hydrogen atom, an alkyl group at C₁ to C₅, an allyl or propargyl group, R₁ represents a hydrogen atom or an —OH group, and X is a nitrogen atom or a —CH— group, said modified deoxycytidine having pairing properties close to those of the natural cytidine it replaces.

Among the modified deoxycytidines of formula (I) above, mention may be made of the following compounds: N-4-methyl-2'-deoxycytidine (d^{4Me}C), N-4-ethyl-2'-deoxycytidine (d^{4Et}C), N-4-propyl-2'-deoxycytidine (d^{4Pro}C), N-4-allyl-2'-deoxycytidine (d^{4Allyl}C), N-4-propargyl-2'-deoxycytidine (d^{4Propargyl}C), 1-B-D-arabinofuranosyl-cytosine (d^{Ara}C), 6-azadeoxycytidine (d^{6N}C).

The nucleic acids comprising dC*s in the place of dCs can be used to produce hybridisation complexes with complementary nucleic acid sequences whose natural deoxycytides dC have also been replaced by modified nucleosides dC*, in order to produce hybridisation complexes in which the stability of all the base pairs C*-G is close to that of the non-modified base pairs A-T. The natural deoxycytidines may be replaced by dC*s as defined above using any method known to Men of the Art, such as an enzymatic polymerisation reaction using dC* nucleosides.

A second type of base which may be contained in the composition of said first and/or second nucleic acid molecule is a modified deoxyguanosine meeting the following formula:

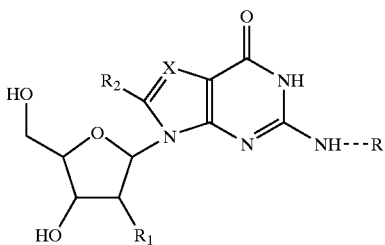

(II)

in which R represents a hydrogen atom or an alkyl group at C₁ to C₅, an allyl or propargyl group, R₁ represents a hydrogen atom or a bromine atom, and X is a nitrogen atom or a —CH— group, said modified deoxyguanosine having pairing properties close to those of the natural deoxyguanosine it replaces.

Among the modified deoxyguanosines of formula (II) above, mention may be made of the following compounds: N-2-methyldeoxyguanosine (d^{2Me}G), N-2-propyldeoxyguanosine (d^{2Pro}G), N-2-isopropyldeoxyguanosine (d^{2IsoPro}G), N-2-ethyldeoxyguanosine (d^{2Et}G), 7-deazadeoxyguanosine (d^{7c}G), 8-bromo-deoxyguanosine (d^{8Br}G).

The nucleic acids comprising dG*s in place of dGs can be used to produce hybridisation complexes with complementary nucleic acid sequences, whose natural deoxyguanosines dG have also been replaced by modified nucleosides dG*, in order to produce hybridisation complexes in which the stability of all the base pairs G*-C is close to that of the non-modified base pairs A-T. The natural deoxyguanosines present in the target nucleic acid sequence may be replaced by dG*s as defined above, using any method known to Men of the Art, such as an enzymatic polymerisation reaction using dG* nucleosides.

A third type of base which may be contained in the composition of said first and/or second nucleic acid molecule is a modified deoxyuridine meeting the following formula:

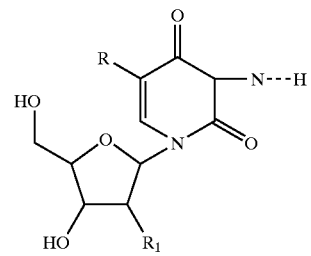

(III)

in which R₁ represents a hydrogen atom or an —OH group, R represents a group with the formula —C≡CH, or —C≡C—CH3, said modified deoxyuridine having pairing properties close to those of the natural thmyidine it replaces.

Among the modified deoxyuridines of formula (III) above, mention may be made of the following compounds: 5-ethynyldeoxyuridine (d^{5Ethynyl}U), 5-propynyldeoxyuridine (d^{5Propynyl}U).

The nucleic acids comprising dU*s in place of the Ts can be used to produce hybridisation complexes with complementary nucleic acid sequences, in which the natural thymidines T have also been replaced by modified nucleosides dU*, in order to produce hybridisation complexes in which the stability of all the base pairs U*-A is close to that of the non-modified base pairs G-C. The natural thymidines present in the target nucleic acid sequence may be replaced by the dU*s defined above using any method known to Men of the Art, such as an enzymatic polymerisation reaction using dU* nucleosides.

A fourth type of base which may be contained in the composition of said first and/or second nucleic acid molecule is a modified deoxyadenosine with the formula:

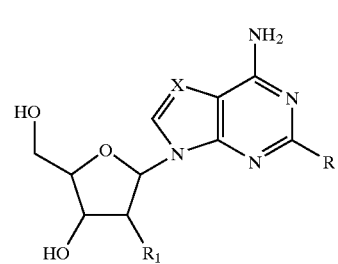

(IV)

in which R₁ represents a hydrogen atom or an —OH group, R represents a hydrogen atom or a NH2 group, X is chosen from among a nitrogen atom, groups with the formula: C—Br, C—Cl, C—C≡CH, C—C≡C—CH3, said modified deoxyadenosine having pairing properties close to those of the natural deoxyadenosine it replaces.

Among the modified deoxyuridines of formula (IV) above, mention may be made of the following compounds: 1'amino-2-deoxyadenosine ($d^{2NH_2}A$), 7-deaza-7-bromodeoxyadenosine, 7-deaza-7-propynyl-deoxyadenosine, 1'amino-2-7-deaza-7-bromodeoxyadenosine, 1'amino-2-7-deaza-7-propynyl-deoxyadenosine.

The nucleic acids comprising dA*s in place of dAs can be used to produce hybridisation complexes with complementary nucleic acid sequences in which the natural deoxyadenosines dA have also been replaced by modified dA* nucleosides in order to produce hybridisation complexes in which the stability of all the base pairs A*-U or A*-T is close to that of the non-modified base pairs G-C. The natural deoxyadenosines present in the target nucleic acid sequence may be replaced by the dA*s defined above using any method known to Men of the Art, such as an enzymatic polymerisation reaction using dA* nucleosides.

Advantageously, in the method of the invention the first and second nucleic acid molecules are of deoxyribonucleic type.

According to an embodiment of particular interest of the methods of the invention for producing a hybridisation complex and for the assay of the nucleic acid sequences, the contacting of the first and second nucleic acid molecules under conditions allowing a specific hybridisation complex to be produced, is conducted in the presence of tetramethylammonium chloride or a functionally equivalent derivative thereof, such as the halides of trimethylalklylammonium. With this type of medium it is possible to adjust the stabilisation of the pairs which may or may not comprise modified bases.

The invention also relates to a hybridisation complex produced from two complementary, or substantially complementary, nucleic acid molecules, whose stability is substantially independent of the base composition of the two hybridised nucleic acid molecules, characterized in that at least one of the types of base pair contained in the composition of said complex comprises at least one modified base having pairing properties close to those of the natural base it replaces, such that the totality of the base pairs contained in the composition of said complex is of like stability.

In accordance with a first preferred embodiment, the hybridisation complex of the invention is characterized in that the same type of base contained in the sequence of the first and second nucleic acid molecule is a modified base having pairing properties close to those of the natural base it replaces. In this embodiment the invention gives particular consideration to cases in which:

the hybridisation complex is characterized in that one of the four types of base contained in the sequence of the first and second nucleic acid molecule is a modified base having pairing properties close to those of the natural base it replaces, such that one of the two types of base pair contained in the composition of the complex comprises a modified base;

the hybridisation complex is characterized in that two of the four types of bases contained in the sequence of the first and second nucleic acid molecule are modified bases having pairing properties close to those of the natural bases they replace, such that the two types of base pair contained in the composition of the complex comprise modified bases.

According to a second preferred embodiment, the hybridisation complex of the invention is characterized in that two of the four types of bases contained in only one of the first and second nucleic acid molecules, are modified bases having pairing properties close to those of the natural bases they replace, such that one of the two types of base pair contained in the composition of the complex comprises a modified base.

Advantageously, the first or second nucleic acid molecule forming the hybridisation complex of the invention is an oligonucleotide probe.

The chemical modifications of the nucleosides dC, dG, T and dA contained more particularly in the composition of said first and/or second nucleic acid molecule of the complexes of the invention are those described previously for modified deoxycytidine, modified deoxyguanosine, modified deoxyuridine and modified deoxyadenosine.

Other advantages and characteristics of the invention will become apparent on reading the following examples given for guidance purposes and are not restrictive, which relate to the preparation of modified nucleosides, their use in the preparation of modified nucleic acids and the use of the latter to prepare hybridisation complexes whose stability is substantially independent of the base composition.

I—Preparation of Modified Nucleosides

1) General Outlines

The 3' phosphoramidites of modified nucleosides are commercially available, for example:

5'-0-dimethoxytrityl-3'-0-(2-cyanoethyl-N,N-diisopropylamidophosphite)-1-B-D-arabinofuranosyl-cytosine (Glen research), 5'-0-dimethoxytrityl-3'-0-(2-cyanoethyl-N,N-diisopropylamidophosphite)-5-propynyl-2'-deoxyuridine (Glen Research), 5'-0-dimethoxytrityl-3'-0-(2-cyanoethyl-N,N-diisopropylamidophosphite)-7-deaza-2'-deoxyguanosine (Glen Research), 5'-0-dimethoxytrityl-3'-0-(2-cyanoethyl-N,N-diisopropylamidophosphite)-8-bromo-2'deoxyguanosine (Glen Research).

The other phosphoramidites of modified nucleosides may also be prepared in the laboratory using other nucleosides modified with techniques described in the literature (N. D. Sinha et al., *Nucleic Acid Res.*, 1984, 12, 4539–4557; J. Nielsen et al. *Nucleic Acid Res.*, 1986, 14, 7391–7403).

The synthesis of 5'-O-dimethoxytrityl-3'-O-(2-cyanoethyl-N,N-diisopropylamidophosphite)-N-4-alkyl-2'-deoxycytidine is made from commercial 2'-deoxycytidine (Aldrich). It comprises protecting the 5' and 3' hydroxyls from 2' deoxyuridine through the action of dimethoxytrityl chloride and tert-butyldimethlsilsyl chloride respectively. The conversion of 2'-deoxyuridine into N-4-alkl-2'-deoxycytidine is made during a first stage by activation of the C4 position of 2'-deoxyuridine protected by treatment with phosphorus oxychloride in the presence of triazole, followed by treatment with the corresponding primary amines. After deprotecting the 3' hydroxyl through the action of tetrabutylammonium fluoride, the phosphitylation of position 3' is made using 2-cyanoethyl-N,N-diisopropylamidochlorophosphite.

The synthesis of 5'-O-dimethoxytrityl-3'-O-(2-cyanoethyl-N,N-diisopropylamidophosphite)-6-aza-2'-deoxycytidine is made, for example, using commercial 6-aza-uridine (Sigma), which is deoxygenated at position 2' then converted into 6-aza-2'deoxycytidine. The selective protection of the hydroxyls at 5' and 3' of 6-aza-uridine is made through the action of tetraisopropyldisiloxane chloride. After activation of the hydroxyl at 2' with phenoxythiocarbonyl chloride, deoxygenation is conducted with tin tributyl in the presence of α, α azoisobutyronitrite (M. J. Robins and J. S. Wilson, *Am. Chem. Soc.*, 1981, 103, 932–933). The conversion of 6-aza-deoxyuridine into 6-azadeoxycytidine is made during a first stage by activation at position $C_4$ of 6-aza-deoxyuridine through treatment with phosphorus oxychloride in the presence of triazole followed by treatment with gaseous ammonia (M. Perbostand and Y. S. Sanghvi, *J. Chem. Soc. Perkin. Trans.*, 1, 1994, 2051–2052). The amino exocyclic group is then protected by benzoylation. After deprotecting the 5' and 3' hydroxyls, the 5' hydroxyl is protected by tritylation, and phosphitylation of position 3' is made using 2-cyanoethyl-N,N-diisopropylamidochlorophosphite.

The synthesis of 5'-O-dimethoxytrityl-3'-O-(2-cyanoethyl-N,N-diisopropylamidophosphite)-N-2-alkyl-2'-deoxyguanosine was made using an 8-step process (T. Steinbrecher, C. Wameling, F. Oesh and A. Seider, *Angew. Chem. Int. Eng.* 1993, 32, 404–406). The first step comprises protecting the carbonyl at position 6 according to Mitsunobu's reaction using p-nitrophenyl-ethanol. Deamination of position 2 by treatment with sodium nitrite leads to the hydroxyl compound. The 5' and 3' hydroxyls are then protected respectively with the dimethoxytrityl and acetyl groups. The hydroxyl at position 2 is then converted into an ester of sulphonic trifluoromethane acid. The treatment of the latter with an amine (methylamine, ethylamine . . . ) leads to the corresponding compound N-2-alkyl-2'-deoxyguanosine. After deprotecting the hydroxyl at 3', the phosphitylation of the latter with 2-cyanoethyl-N,N-diisopropylamidochlorophosphite leads to the desired phosphoramidite.

2) Experimental Examples

EXAMPLE 1

Preparation of 5'O-dimethoxytrityl-3'-O-(2-cyanoethyl-N,N-diisopropylamidophosphite)-N-4-ethyl-2'-deoxycytidine a) Preparation of 5'-O-dimethoxytrityl-2'-deoxyuridine.

To 5 g (0.0219 mole) of 2' deoxyuridine previously dried by coevaporation with anhydrous pyridine (3 times) then placed in solution in 80 ml anhydrous pyridine, are added 8.2 g (0.024 mole) of dimethoxytrityl chloride at 0° C. The progress of the reaction is monitored by MCC. After 2 hours' reaction at room temperature, MCC of the mixture shows that the reaction is complete. The excess dimethoxytrityl chloride is destroyed through the addition of 2 ml of methanol. The mixture is concentrated in a vacuum, recovered with dichloromethane and washed with a 5% solution of sodium bicarbonate (2 times) then with water. The organic phase is dried on sodium sulphate and the solvent dispelled under a vacuum. The residue is purified by precipitation with hexane. A white precipitate is obtained. This compound is recovered by filtration and dried in a dessicator.

Yield=77% (9 g). MCC Merck silica gel 60F 254. Rf=0.40 [eluant: $CH_2Cl_2$/MeOH (95:5, v/v)]=Syst A. Rf=0.77 [eluant: $CH_2Cl_2$/MeOH (90:10, v/v]=Syst B.

b) Preparation of 5'-O-dimethoxytrityl-3'-O-(tert-butyldimethylsilyl)-2'-deoxyuridine.

9 g of 5'-O-dimethoxytrityl-2'-deoxyuridine (0.016 mole) and 3.26 g of imidazole (0.048 mole) are dried by coevaporation with anhydrous pyridine (3 times) and placed in solution with 100 ml of anhydrous pyridine. 3.13 g of tert-butyldimethylchlorosilane (0.02 mole) are added. The reaction is monitored by MCC. After 12 hours' reaction, at room temperature, the mixture is recovered with dichloromethane. The organic phase is washed with a 5% solution of sodium bicarbonate (2 times) then dried on sodium sulphate. The medium is concentrated and cold precipitated in hexane. The precipitate obtained is filtered under the vacuum of the water pump and dried in the dessiccator.

Yield=71% (7.7 g). MCC Merck silica gel 60F 254, Rf=0.57 syst A, Rf=0.86 syst B.

c) Preparation of 5'-O-dimethoxytrityl-3'-O-(tert-butyldimethylsilyl)-N-4-ethyl-2'-deoxycytidine To 3.1 g of triazole (0.047 mole) previously dried 3 times by coevaporation with anhydrous acetonitrile, solubilised in 50 ml of acetonitrile, are added to 0° C. 0.98 ml of $POCl_3$ (0.01 mole) and 7.3 ml of triethylamine (0.052 mole). The reaction mixture is maintained under stirring for 30 minutes at 0° C. Then 2 g of 5'-O-dimethoxytrityl-3'-O-(tert-butyldimethylsilyl)-2'-deoxyuridine (0.0031 mole) previously dried by coevaporation with anhydrous acetonitirile and solubilised in 10 ml of acetonitrile are added to the reaction medium. The reaction mixture is then brought to room temperature and magnetically stirred for 4 hours.

On the crude triazole derivative obtained (Rf=0.55 syst A, Rf=0.91 syst B) are added 9.6 ml) of an ethylamine solution (16 M in acetonitrile, 0.15 mole). The reaction is monitored under MCC and the initial compound is seen to disappear entirely after 2 hours. The medium is then concentrated under reduced pressure, recovered with dichloromethane and washed in water. After drying on sodium sulphate, the solvent is dispelled and purification on a silica gel column in the system [eluant: $CH_2Cl_2$/MeOH/$Et_3$N/98:1:1, v/v at (97:2:2] achieves isolation of 1.7 g of the desired product.

Yield=81%. MCC Merck silica gel 60F 254, Rf=0.26 syst A. Rf=0.70 syst B.

d) Preparation of 5'-O-dimethoxytrityl-N-4-ethyl-2'-deoxycytidine 1.7 g of 5'-O-dimethoxytrityl-3'-O(tert-butyldimethylsilyl)-N-4-ethyl-2-deoxycytidine (0.0025 mole) are treated with 5 ml of a 1M solution of tetrabutylammonium fluoride in tetrahydrofurane (0.005 mole) at room temperature. The reaction monitored by MCC is complete after 2 hours. The medium is concentrated under reduced pressure then recovered with dichloromethane and washed in a solution of sodium bicarbonate and concentrated under reduced pressure. The residue is purified on a silica gel column in the system [eluant: $CH_2Cl_2$/MeOH (98:2, v/v) at 95:2:5, v/v].

Yield=78% (1.1 g). MCC Merck silica gel 60F 254, Rf=o.55 syst B.

e) Preparation of 5'-O-dimethoxytrityl-3'-O-(2-cyanoethyl-N,N-diisopropylamidophosphite)-N-4-ethyl-2'-deoxycytidine 5'-O-dimethoxytrityl-N-4-ethyl-2'-deoxycytidine is dried by 3 successive coevaporations with anhydrous acetonitrile then left overnight in the dessiccator. To 200 mg (0.35 mole) of 5'-O-dimethoxy-trityl-N-4-ethyl-2'-deoxycytidine deoxycytidine solubilised in 4 ml of dichloromethane (anhydrous and passed through basic alumina) are added, under stirring and in an inert atmosphere 0.24 ml of distilled diisopropylethylamine (1.43 mole) followed, drop by drop, by 0.12 ml (0.53 mole) of 2-cyanoethyl-N,N-diisopropylamidochlorophosphite. After one hour, the reaction is complete. To the reaction mixture are then added 20 ml of ethyl acetate, followed by washing with a 10% solution of sodium bicarbonate then with a saturated NaCl solution. After extraction, the organic phase is dried on sodium sulphate and concentrated. The residue is purified on a column of silica gel in the system [eluant: $CH_2Cl_2$/AcOEt/$Et_3$N, (60:30:10, v/v]. The compound is then precipitated in hexane at −70° C. and recovered by quick filtration and dried in a dessiccator.

Yield=48% (130 mg). MCC Merck silica gel 60F 254, Rf=0.35 and 0.33 syst A; Rf=0.68 and 0.61 syst C.

EXAMPLES 2 TO 5

By operating as in stage (c) of example 1, and by replacing the ethylamine by the methylamine, propylamine, allylamine and propargylamine, it was possible to obtain respectively 5'-O-dimethoxytrityl-3'-O-(tert-butyldimethylsilsyl)-N-4-methyl-2'-deoxycytidine (compound 2c), 5'-O-dimethoxytrityl-3'-O-(tert-butyldimethylsilsyl)-N-4-propyl-2'-deoxycytidine (compound 3c), 5'-O-dimethoxytrityl-3'-O-(tert-butyldimethylsilsyl)-N-4-allyl-2'-deoxycytidine (compound 4c), 5'-O-dimethoxytrityl-3'-O-(tert-butyldimethylsilsyl)-N-4-propargyl-2'-deoxycytidine (compound 5c), whose characteristics are summarised in table I below.

TABLE I

| Compounds | Yield % | Rf syst A | Rf syst B |
| --- | --- | --- | --- |
| 2c | 49 | 0.22 | 0.68 |
| 3c | 61 | 0.23 | 0.72 |
| 4c | 69 | | |
| 5c | 70 | | |

Then by operating as in stage (d) of example 1, using the above compounds 2c, 3c, 4c and 5c, the corresponding compounds 2d, 3d, 4d, and 5d are obtained whose characteristics are summarised in table II below.

TABLE II

| Compounds | Yield % | Rf syst B |
| --- | --- | --- |
| 2d | 78 | 0.53 |
| 3d | 84 | 0.59 |
| 4d | 90 | 0.63 |
| 5d | 72 | 0.64 |

Finally the following phosphoramidites 2e, 3e, 4e and 5e of formula (V):

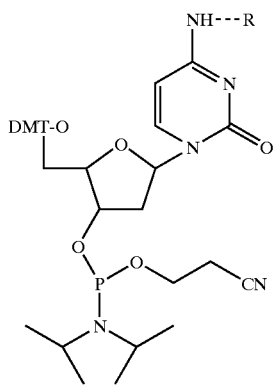

are obtained using the above compounds 2d, 3d, 4d and 5d by operating as in stage (e) of example 1. The characteristics of these compounds are summarised in table III below which also gives the signification of R.

TABLE III

| Compounds | Yield % | Rf syst A | Rf syst C |
| --- | --- | --- | --- |
| 2e | 46 | 0.36 | 0.52 |
| R = —CH$_3$ | | 0.32 | 0.43 |
| 3e | 47 | 0.39 | 0.73 |
| R = -nC$_3$H$_7$ | | 0.34 | 0.68 |
| 4e | 42 | 0.35 | 0.72 |
| R = —CH$_2$—CH=CH$_2$ | | 0.30 | 0.67 |
| 5e | 49 | 0.35 | 0.75 |
| R = —CH$_2$C≡CH | | 0.31 | 0.69 |

[eluant: CH$_2$Cl$_2$/AcOEt/Et$_3$N, (45:45:10, v/v] = syst C.

EXAMPLE 6

Preparation of 5'-O-dimethoxytrityl-3'-O-(2-cyanoethyl-N,N-diisopropylamidophosphite)-6-aza-deoxycytidine This compound was obtained in 6 stages using 6-aza-uridine.

The synthesis of 5'-O-dimethoxytrityl-3'-O-(2-cyanoethyl-N,N-diisopropylamide-phosphite)-6-aza-deoxycytidine is conducted for example using commercial 6-aza-uridine which is deoxygenated at position 2' then converted into 6-aza-2'-deoxycytidine. The selective protection of the 5' and 3' hydroxyls of 6-aza-uridine is made through the action of tetraisopropyldisiloxane. After activation of the 2' hydroxyl with phenoxythiocarbonyl chloride, deoxygenation is conducted with tin tributyl in the presence of α, α azoisobutyronitrite (M. J. Robins and J. S. Wilson, *J. Am. Chem. Soc.*, 1981, 103, 932–933). The conversion of 6-azadeoxyuridine into 6-azadeoxycytidine is made during a first stage through activation of position C4 of &-azadeoxyuridine by treatment with phosphorus oxychloride in the presence of triazole, followed by a treatment with gaseous ammonia (M. Perbostand and Y. S. Sanghvi, *J. Chem. Soc. Perkin. Trans.* 1, 1994, 2051–2052). The amino exocyclic group is then protected by benzoylation. After deprotecting the 5' and 3 hydroxyls by treatment with tetrabutylammonium fluoride in tetrahydrofurane, the 5' hydroxyl is protected by the dimethoxytrityl group and phosphitylation of position 3' is conducted using 2-cyanoethyl-N,N-diisopropylamidochlorophosphite as in example 1 stage (e).

MCC Merck silica gel 60 F 254, Rf=0.37 and 0.43 syst A.

EXAMPLES 7 TO 10

Preparation of 5'-O-dimethoxytrityl-3'-O-(2-cyanoethyl-N,N-diisopropylamido-phosphite)-N-2-alkyl-2'-deoxyguanosine The synthesis of 5'-O-dimethoxytrityl-3'-O-(2-cyanoethyl-N,N-diisopropylamidophosphite)-N-2-alkyl-2'-deoxyguanosine was conducted for example in 8 steps according to T. Steinbrecher, C. Wameling, F. Oesh and A. Seider (*Angew. Chem. Int. Engl.* 1993, 32, 404–406). It consists, during a first stage, of protecting the carbonyl at position 6 of the deoxyguanosine according to Mitsunobu's reaction using p-nitrophenyl-ethanol. Deamination of position 2 by treatment with sodium nitrite leads to the hydroxyl compound. The hydroxyls 5' and 3' are then protected with the dimethoxytrityl and acetyl groups respectively. The hydroxyl at position 2 is then converted into an ester of sulphonic trifluoromethane acid. The treatment of the latter with an amine (methylamine, ethylamine, propylamine, isopropylamine . . . ) leads to the corresponding compound N-2-alkyl-2'-deoxyguanosine. After deprotecting the 3' hydroxyl, phosphitylation of the latter with the 2-cyanoethyl-N,N-diisopropylamidochlorophosphite as in example 1, stage (e) leads to the desired phosphoramidite of formula (VI):

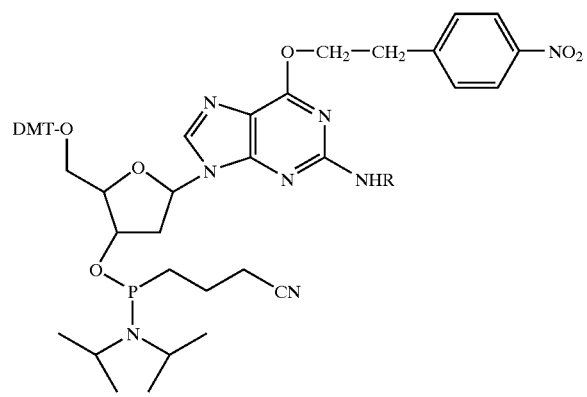

in which R=Methyl (compound of example 7), R=Ethyl (compound of example 8), R=Propyl (compound of example 9), R=Isopropyl (compound of example 10).

II—Preparation of the Modified Oligonucleotides

The oligonucleotides comprising modified bases, and designated as modified oligonucleotides, may be prepared in solution or on a solid support according to conventional processes for the synthesis of oligonucleotides using the phosphotriester method (J. Stawinski et al., *Nucleic Acids Res.*, 1977, 4, 356–371) the chemistry of phosphoramidites (S. L. Beaucage, M. H. Caruthers, *Tetrahedron Lett.* 1981, 22, 1859–1862) or the chemistry of H-phosphonates (P. J. Garegg et al., *Tetrahedron Lett.* 1986, 27, 4055–4058). The modified oligonucleotides may be conveniently made on a solid support.

The assembly of the bases is made in an oligonucleotide synthesizer on a CPG support (Controlled Pore Glass) functionalised with a nucleoside using the phosphoramidite method described by Beaucage and Caruthers. The syntheses are conducted on micromole scale using ten equivalents of commercial phosphoramidites and modified phosphoramidite(s) prepared as indicated in examples 1 to 10, per cycle. The length of the cycle is in the region of 10 minutes with a coupling time of 1.5 minutes for the phosphoramidites of natural nucleosides. The coupling time for the phosphoramidite of modified nucleosides was extended by one minute. At the end of the synthesis an additional detrytilation stage was carried out to free the terminal primary alcohol function. Deprotection is conducted with a concentrated ammonia solution at 50° C. and left overnight. Extraction with ethyl acetate removes the soluble organic compounds. After extraction, the aqueous solution is recovered and concentrated and the products are subsequently purified by HPLC.

Table IV below gives the retention times (RT) of some prepared oligonucleotides.

TABLE IV

| Examples | RT in minutes (syst A) | RT in minutes (syst B) |
| --- | --- | --- |
| 11 d (CGA CGA CGA) | 25.6 | 12.3 |
| 12 d (CGA $^{4Me}$CGA CGA) | 25.2 | 12.16 |
| 13 d (CGA $^{4Et}$CGA CGA) | 26.8 | 12.9 |
| 14 d (CGA $^{4Pro}$CGA CGA) | 25.2 | 13.03 |
| 15 d (CGA $^{4Allyl}$CGA CGA) | 25.4 | 12.81 |
| 16 d CGA $^{4Propargyl}$CGA CGA) | 25.2 | 12.78 |

In system (a) the assays of the oligomers by ion exchange are made on Pharmacia Fine Chemicals FPLC equipment (GP 250/P 3500) with a DEAE Waters column (Protein-Pak™, DEAE 8HR (10 mm×100 mm). The gradients used are salt gradients (NaCl): 2 minutes at 0% at B; from 0 to 30% at B in 40 minutes; flow: 1 ml/min. A: 25 mM Tris, 10% $CH_3CN$, pH=8; buffer A+1.5 M NaCl.

In system (b) the assays in reversed phase are made on a Waters 625 LC System apparatus equipped with a Waters 990 photoiodine detector and a Merck column, LichroCart (125 mm×4 mm) filled with Lichorspher 100 RP-18 (5 μm). The eluants are water/acetonitrile mixtures with 0.1 M triethylammonium acetate (TEAA), pH=7. A contains 5% $CH_3CN$ and B contains 80% $CH_3CN$. $CH_3Ch$ gradients are made; from 0% to 20% at B in 20 minutes. The flows of these eluants are 1 ml/minute.

The presence and the proportions of nucleosides in the sequences were verified by enzymatic hydrolysis through action of the endonuclease $P_1$, then in a second stage through the action of the alkaline phosphatase (AP) in accordance with the following protocol:

To 1 DO of oligonucleotide are added 50 μl of a buffer solution of $CH_3COO^-Na^+$ pH=5.33 and $ZnSO_4$ (0.1 M) and 10 μl of a nuclease solution $P_1$. The reaction is left in a water bath for 2 hours at 37° C. The pH of the hydrolysate is then adjusted to pH 9 with a 1M Tris solution. Then 10 μl of alkaline phosphatase are added to the mixture and incubated for 2 hours at 37° C. The enzyme is then destroyed under heat by boiling the solution for 1 to 2 minutes. The different compounds formed are then identified and quantified by reversed phase with the following gradient: 0% at B for 5 minutes; from 0% to 9% at B for 15 minutes. A: 0.1M TEAA, 2% $CH_3CN$; B: 0.1M TEAA, 80% $CH_3CN$. Flow=1 ml/min.

By way of example, the enzymatic hydrolysis of oligonucleotide N• 13 conducted along the following pattern:

$d^5$[CpGpAp$^{4Et}$CpGApCpGpA] 3'

¬P1 dC+pdG+pdA+pd$^{4Et}$C+pdG+pdA pC+pdG+pdA

¬PA

2dC+3dG+3dA (Ø3dI)_+d$^{4Et}$C led to: 2dC+3dG+3dA+d$^{4Et}$C, of which table V below gives the retention times (RT) of each nucleoside (Retention time in reversed phase on column $C_{18}$).

TABLE V

| Nucleosides | RT (minutes) |
|---|---|
| dC | 2.68 |
| dI | 5.93 |
| dG | 7.20 |
| d$^{4Et}$C | 9.75 |

The mass of oligonucleotides N•11 to 16 was checked by mass spectrometry using the MALDI technique (Matrix-Assisted Laser desorption); Lasermat apparatus by Finnigan) using dT$_{12}$ as reference and 1 µl of a constituted mixture. 10 µl of a 0.5 M solution of 2,4,6-trihydroxy acetophenone in ethanol, 5 µl of a 0.1 M aqueous solution of diammonium-L-tartarate and 1 µl of an aqueous solution (10 DO/ml) of the sample to be assayed were deposited on a target and the solvents removed by evaporation.

Using the same operating method as previously, the oligonucleotides given in table VI below were prepared using phosphoramidites of natural deoxynucleosides and phosphoramidites of nucleosides modified in the laboratory or obtained commercially.

stage concerns the preparation of the modified deoxynucleosides 5' monophosphates by reaction of the modified nucleosides with phosphorus oxychloride in trialkylphosphate (M. Yoshikawa, T. Kato and T. Takenishi, *Tetrahedron Lett.*, 1967, 5055–5068). The second stage concerns the activation of 5'-phosphate by reaction with carbonyldiimidazole then coupling of the intermediary activated with the salt of pyrophosphate tributylammonium in accordance with D. E. Hoard and D. G. Ott (*J. Amer. Chem. Soc.* 1965, 87, 1785–1788).

In the case of derivatives of N-4-alkyldeoxycytidine, the triphosphates may be obtained from deoxycytidine triphosphate by transamination in the presence of alkylamine and bisulphite (P. S. Miller and C. D. Cushman, 1992 *Bioconjugate Chem.* 3, 74–79).

IV—Hybridisation Property of Modified Oligonucleosides Comprising a Modified Deoxycytidine (dC*) with Natural DNA Sequences Hybridisation studies were conducted using a KONTRON UVIKON absorption spectrometer with a 941 to 260 nm cell changer.

Half transition temperature measurements Tm of the series of natural nonanucleotides modified with natural

TABLE VI

| SEQ ID NO: | | | | | | | | | | | |
|---|---|---|---|---|---|---|---|---|---|---|---|
| 1 | 5' | C | G | A | 4Me C | G | A | C | G | A | 3' |
| 2 | 5' | C | G | A | 4$^E$t C | G | A | C | G | A | 3' |
| 3 | 5' | C | G | A | 4Pro C | G | A | C | G | A | 3' |
| 4 | 5' | C | G | A | 4Allyl C | G | A | C | G | A | 3' |
| 5 | 5' | C | G | A | 4Propargyl C | G | A | C | G | A | 3' |
| 6 | 5' | C | G | A | Ara C | G | A | C | G | A | 3' |
| 7 | 5' | C | G | A | 4Me C | G | A | 4Me C | G | A | 3' |
| 8 | 5' | C | G | A | 4$^E$t C | G | A | 4$^E$t C | G | A | 3' |
| 9 | 5' | C | G | A | Pro C | G | A | Pro C | G | A | 3' |
| 10 | 5' | C | G | A | Ara C | G | A | ara C | G | A | 3' |
| 11 | 5' | A | 4Et C | A | A | 4$^E$t C | A | A | 4Et C | A | 3' |
| 12 | 5'T T | T | 4me C | G | T | 4Me C | G | T | 4Me C | G | T T 3' |
| 13 | 5' | 4Me C | G | A | 4Me C | G | A | 4Me C | G | A | 3' |
| 14 | 5'T T | T | 4Et C | G | T | 4$^E$t C | G | T | 4Et C | G | T T 3' |
| 15 | 5' | 4Et C | G | A | 4Et C | G | A | 4Et C | G | A | 3' |
| 16 | 5'T T | T | 4Et C | G | T | 4$^E$t C | T | T | 4Et C | G | T T 3' |
| 17 | 5'T T | 5Propynyl U | 5Propynyl U | A | 5Propynyl U | 5Propynyl U | A | 5Propynyl U | 5Propynyl U | A | T T 3' |
| 18 | 5' | 5Propynyl U | A | A | 5Propynyl U | A | A | 5Propynyl U | A | A | 3' |
| 19 | 5'T T | 4Me C | 4Me C | A | 4Me C | 4Me C | A | 4Me C | 4Me C | A | T T 3' |
| 20 | 5' | 4Me C | G | G | 4Me C | G | G | 4Me C | G | G | 3' |
| 21 | 5' | C | G | A | C | 7C G | A | C | G | A | 3' |
| 22 | 5' | C | G | A | C | I | A | C | G | A | 3' |
| 23 | 5' | C | G | A | C | 2$^E$t G | A | C | G | A | 3' |
| 24 | 5' | C | G | A | C | 2Pro G | A | C | G | A | 3' |
| 25 | 5' | C | G | A | C | 2iPro G | A | C | G | A | 3' |
| 26 | 5' | C | G | A | C | 42iButyryl G | A | C | G | A | 3' |

III—Preparation of the DNA to be Assayed

The fragments of nucleic acid to be assayed made up of natural nucleosides and modified nucleoside(s) may be obtained with the PCR genetic amplification technique using a mixture of triphosphates of natural nucleosides and modified nucleoside(s). These compounds may also be obtained, during a first stage, by preparing fragments of monocatenary natural DNA using the asymmetric PCR technique, then during a second stage by copying the fragment of natural monocatenary DNA in a complementary sequence made up of natural nucleosides and modified nucleoside(s) using a mixture of triphosphates of natural deoxynucleosides and modified nucleotide(s) and polymerase DNA.

The modified deoxynucleosides 5' triphosphates may be prepared from modified deoxynucleosides in two stages as for the natural triphosphate deoxynucleosides. The first tridecadeoxynucleotides were carried out with $2.10^{-6}$ M solutions of oligonucleotides in a buffer of $10^{-2}$ M sodium cacodylate at pH 7 and containing $2.10^{-4}$ M EDTA and 1 M sodium chloride. The temperature rise takes place from 0° C. to 60° C. at the rate of 0.5° C. per minute. These conditions will be identical for the examples of FIGS. 1 to 12 and for FIG. 13 in part.

FIGS. 1 and 2 show the Tm values of the double strands formed by natural tridecadeoxynucleotides with natural nonadeoxynucleotides and with nonadeoxynucleotides comprising a modified deoxycytidine dC*.

The Tm values in FIG. 1 show that for the double strands made of natural nucleotides, hybrid stability varies greatly with base composition. Therefore the replacement of the pair A-T at position 4 of double strand 1 (Tm=46.1° C.) by a G-C pair leads to an increase in Tm of +5.2° C. (double strand 2, Tm=51.3° C.); on the other hand, replacing this same pair A-T by a G-C* pair (in particular for C*=N-ethyl-dC) leads to obtaining hybrids whose stability [C*=N-4-ethyldeoxycytidine, duplex 4 (Tm=47.2° C.)] is equivalent to that of duplex 1.

This hybridisation property of the G-C$^{4Et}$ pair is maintained when the latter is inserted in the place of the A-T pair at positions 4 and 7 of double strand 9 (FIG. 2; duplex 9, Tm=41.1° C.; duplex 11, Tm=41.7° C.). As expected, replacement of the A-T pair by the G-C pair (FIG. 2) at positions 4 and 7 leads to an increase in Tm in the region of 10° C.

To illustrate that the formation of duplexes comprising the G-C* pair is specific, hybridisation studies of the modified nonamers $^{3'}$AGCAGC*AGC$^{5'}$ (SEQ ID NO: 27) with the DNA sequences $^{5'}$dTTTCGTCATCGTT$^{3'}$ (SEQ ID NO: 28), $^{5'}$dTTTCGTCCTCGTT$^{3'}$ (SEQ ID NO: 29), $^{5'}$dTTTCGTCTTCGTT$^{3'}$ (SEQ ID NO: 30) were also conducted. The results given in FIGS. 3, 4 and 5 show that destabilisation due to mismatches of A-C* (duplex 15 to 20 of FIG. 3), C-C* (duplex 22 to 27 of FIG. 4) and T-C* (duplex 29 to 34 of FIG. 5) (for dC*=N-4-methyldeoxycytidine, N-4-ethyldeoxycytidine and 1-b-D-arabinofuranosylcytosine) is equivalent to that of mismatches A-C (duplex 14), C-C (duplex 21) and T-C (duplex 28).

V—Hybridisation Property of Double Strands Made of Base Pairs A-T and G-C$^{4alkyl}$ Studies were conducted on two types of sequences.

In the first type of sequence, the cytosines which are all located on the same strand are replaced by N-ethyldeoxycytosine. The results in FIG. 6 show that the replacement of 3 A-T pairs of duplex 35 (Tm=20° C.) by three G-C$^{4Et}$ pairs leads to duplex 37 with much the same Tm (duplex 37, Tm=27.4° C.), on the other hand the substitution of the same A-T pairs of duplex 35 by G-C pairs, as expected, produced an increase in the region of 21° C. Also, the formation of double strand 37 is specific, as a reduction in Tm of more than 17° C. is observed when there is a mismatch T-C$^{4Et}$ (duplex 38), C-C$^{4Et}$ (duplex 39) or A-C$^{4Et}$ (duplex 41).

In the second type of sequence, the cytosines located on the two strands are replaced by N-4-methylcytosine (duplex 42, FIG. 7) or N-4-ethylcytosine (duplex 43).

The results given in FIG. 7 show that when the 6 A-T pairs of duplex 41 (Tm=18.7° C.) are replaced by 6 G-C pairs (duplex 2, Tm=51.3° C.) the variation in Tm is very high (+32.6° C.); under the same conditions, the use of the base pair G-C* such as G-C$^{4Et}$ can, for example, lead to obtaining duplex 43 whose stability differs little from that of duplex 41.

These results call for the following remarks:

When the nonadeoxynucleotide sequences for example are immobilised on the same solid support, it is not possible to produce specific hybrids at the same time such as duplexes 2 and 41 without the formation of hybrids with mismatch such as duplexes 14, 21 and 28 which have higher Tm values than duplex 41.

the use of duplexes made up of base pairs A-T and G-CN$^{Et}$ can lead to obtaining specific hybrids such as duplexes 41 and 43, for example duplex 44 derived from duplex 43 with, however, a T-C$^{Net}$ mismatch, has very little stability (Tm<10° C.).

VI—Hybridisation Property of Double Strands Comprising Base Pairs A-U$^{5Propynyl}$ and/or G-C$^{4Met}$ The hybridisation properties of duplexes 46 and 47 respectively formed of 9 A-U$^{5Propynyl}$ pairs of 9 G-C$^{4Met}$ pairs were studied and compared with those of the corresponding non-modified duplexes 41 and 45 (FIG. 8).

The results obtained show that duplex 46 which comprises 9 A-U$^{5Propynyl}$ base pairs has an equivalent Tm (duplex 46, Tm=31.2° C.) to that of duplex 47 (Tm=33.3° C.) comprising 9 G-C$^{N4Met}$ pairs, on the other hand duplexes 41 and 45 having the same length and formed respectively of A-T and G-C base pairs give very different Tm values (duplex 41, Tm=18.7° C.; duplex 45, Tm=63.4° C.).

Also, it is seen that the Tm values of the modified duplexes 46 and 47 are located between those of the natural duplexes 41 and 47. It is also seen that the pairing of the A-U$^{5Propynyl}$ pair is specific (duplex 48, Tm=26.1° C.) since a mismatch C-U$^{5Propynyl}$ (duplex 49) or G-U$^{5Propynyl}$ (duplex 50) or T-U$^{5Propynyl}$ (duplex 51) leads to substantial destabilisation.

VII—Hybridisation Property of Oligonucleotides Whose Deoxyguanosines are Partly Replaced by Modified Deoxyguanosines FIG. 9 gives the Tm values of double strands formed between a tridecadeoxynucleotide and nonadeoxynucleotides comprising a modified deoxyguanosine dG*. The results obtained show that the replacement of a natural base pair C-G by a base pair C-G* has an effect on the heat stability of the hybridisation complexes. Among the modified deoxyguanosines used, the substituted derivatives on the amino group at position 2 can allow adjustment of hybrid stability. Therefore the stability of the duplexes containing the base pair C-G$^{2alkyl}$ is reduced whenever the steric hindrance of the substituent increases (duplex 55, 56, 57, 58). Also, the heat stability of duplex 58 comprising the pair C-G$^{2iPr}$ is close to that of duplex 52 containing the pair T-A at the same position.

Also, the pairing of the studied base pairs C-G* is specific (except for C-I); a mismatch A-G* (FIG. 10) or T-G* (FIG. 11) or G-G* (FIG. 12) leads to considerable destabilisation as in the case of A-G or T-G or G-G mismatch.

The results obtained in this example and in examples IV and V show that it is possible to use modified oligonucleotides formed of T, dA, dC$^{4Et}$ and dG$^{2alkyl}$ to produce hybrids, with complementary natural nucleic acid sequences, whose stability is substantially independent of base composition.

VIII—Double Strand Formation Through the Use of Base Pairs A-U$^{5Propynyl}$ and/or G-C in the Presence of Tetramethylammonium Chloride The heat stability of duplexes 41, 45 and 46 comprising 9 base pairs and respectively formed of base pairs A-T, G-C and A-U$^{5Propynyl}$, was studied in a medium containing 1 M NaCl or tetramethylammonium chloride TMACl of variable concentration. The results given in FIG. 13 show that for a given medium the Tm value of duplex 41 made up of 9 A-T base pairs is lower than that of duplex 45 made up of 9 G-C base pairs. On the other hand, in the presence of 3.5 M TMACl the heat stability of duplex 46 (Tm=50.9° C.) formed with 9 base pairs A-U$^{5Propynyl}$ is equivalent to that of duplex 45 (Tm=51.8° C.). In FIG. 13, the Tm values marked "*" correspond to identical experimental conditions to those of the preceding experiments shown in FIGS. 1 to 12, the Tm values marked "**" correspond to the following experimental conditions: $2.10^{-6}$ M oligonucleotides in $50.10^{-3}$ Tris HCl buffer at pH 8 and containing $2.10^{-3}$ M EDTA and tetramethylammonium chloride of varying concentration (2:3:3.5 and 4.4 M).

It is also observed that the pairing of the A-U$^{5Propynyl}$ pair is specific in a 3.5 M TMACl solution (duplex 48, Tm=42.6° C.) as the mismatches C-U$^{5Propynyl}$ (duplex 49, Tm=18.8°

C.) or G-U$^{5Propynyl}$ (duplex 50, Tm=25.7° C.) or T-U$^{5Propynyl}$ (duplex 51, Tm=25.7° C.) lead to considerable destabilisation.

With these results it is possible to use base pairs G-C and A-U$^{5Propynyl}$ to produces duplexes whose stability is both high and is also substantially independent of base composition.

These examples, which are not restrictive, show firstly that oligonucleotides comprising at least one modified base of the invention produce specific hybrids with complementary nucleic sequences, and secondly that the stability of the hybrids produced is substantially independent of the base composition of each strand of the hybrids. Also, with the method of the invention it is possible to make clearer differentiation between perfect hybrids and hybrids with mismatch when several nucleic probes are used at the same time under determined temperature and medium conditions.

What is claimed is:

1. A hybridisation complex which comprises a first nucleic acid molecule hybridized with a second nucleic acid molecule,
wherein the complex comprises:
at least one modified C—G base pair, wherein at least one C or G base contained in the sequence of the first and/or second nucleic acid molecule, or at least one C and G contained in the sequence of the first or second nucleic acid molecule, is a modified base, such that the difference between the melting temperature of:
i.) the complex and
ii) the complex wherein in place of the modified base pair is a naturally-occurring A—T base pair
is less than the difference between the melting temperature of:
i) the complex wherein in the place of the modified base pair is a naturally-occurring C—G base pair and ii) the complex wherein in the place of the modified base pair is a naturally-occurring A—T/U base pair;

or wherein the complex comprises:
at least one modified A—T/U base pair, wherein at least one A or T/U base contained in the sequence of the first and/or second nucleic acid molecule, or at least one A and T/U base contained in the sequence of the first or second nucleic acid molecule, is a modified base, such that the difference between the melting temperature of:
   i.) the complex wherein in place of the modified base pair is a naturally-occurring C—G base pair and
   ii) the complex
is less than the difference between the melting temperature of:
   i) the complex wherein in the place of the modified base pair is a naturally-occurring C—G base pair and
   ii) the complex wherein in the place of the modified base pair is a naturally-occurring A—T/U base pair;

or wherein the complex comprises:
at least one modified C—G base pair and at least one modified A—T/U base pair, wherein at least one C and/or G base and at least one A and/or T/U base contained in the sequence of the first or second nucleic acid molecule is a modified base, or wherein at least one A or T/U base and at least one C or G base contained in the sequence of the first and second nucleic acid molecule is a modified base, wherein the melting temperature of the complex is between:
   (i) the melting temperature of the complex wherein in place of the modified C—G base pair and modified A—T/U base pair are naturally-occurring C—G base pairs, and
   ii) the melting temperature of the complex wherein in place of the modified C—G base pair and modified A—T/U base pair are naturally-occurring A—T/U base pairs.

2. A hybridisation complex in accordance with claim 1, wherein the first or second nucleic acid molecule is an oligonucleotide probe.

3. A hybridisation complex in accordance with claim 1, wherein one of the types of bases contained in composition of said first and/or second nucleic acid molecule is a modified deoxycytidine wherein the modified deoxycytidine has the following formula:

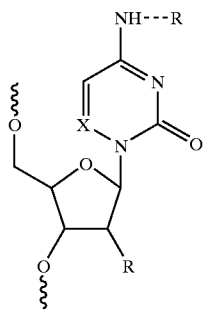

(I)

in which R is selected from the group consisting of a hydrogen atom, an alkyl group at $C_1$ to $C_5$, an allyl group, and a propargyl group; R1 is a hydrogen atom or an —OH group; and X is a nitrogen atom or a —CH— group.

4. A hybridization complex in accordance with claim 3, wherein the modified cytidine of formula (I) is chosen from among: N-4-methyl-2'-deoxycytidine, N-4-ethyl-2'-deoxycytidine, N-4-propyl-2'-deoxycytidine, N-4-allyl-2'-deoxycytidine, N-4-propargyl-2'-deoxycytidine, 1-B-D-arabinofuranosyl-cytosine, and 6-azadeoxycytidine.

5. A hybridisation complex in accordance with claim 1, wherein one of the types of bases contained in the composition of said first and/or second nucleic acid molecule is a modified deoxyguanosine wherein the modified deoxyguanosine has the following formula:

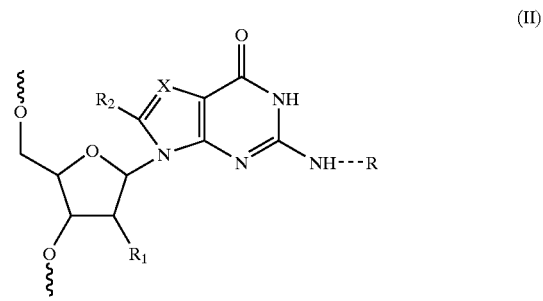

(II)

in which R is selected from the group consisting of a hydrogen atom, an alkyl group at $C_1$ to $C_5$, an allyl group, and a propargyl group; $R_1$ is a hydrogen atom or an —OH group; $R_2$ is a hydrogen atom or a bromine atom; and X is a nitrogen atom or a —CH— group.

6. A hybridization complex in accordance with claim 5, wherein the modified guanosine of formula (II) is chosen from among: N-2-methyldeoxyguanosine, N-2-propyldeoxyguanosine, N-2-isopropyldeoxyguanosine, N-2-ethyldeoxyguanosine, 7-deazadeoxyguanosine, and 8-bromo-deoxyguanosine.

7. A hybridisation complex in accordance with claim 1, wherein one of the types of bases contained in the composition of said first and/or second nucleic acid molecule is a modified deoxyuridine wherein the modified deoxyuridine has the following formula:

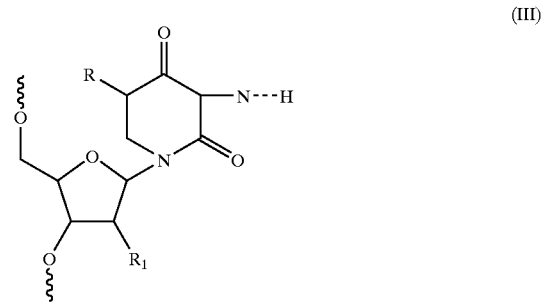

(III)

in which $R_1$ is a hydrogen atom or an —OH group; R is —C≡CH, or —C≡—$CH_3$.

8. A hybridization complex in accordance with claim 7, wherein the modified deoxyuridine of formula (III) is chosen from among: 5-ethynyldeoxyuridine, and 5-propynyldeoxyuridine.

9. A hybridisation complex in accordance with claim 1, wherein one of the types of bases contained in the composition of said first and/or second nucleic acid molecule is a modified deoxyadenosine wherein the modified deoxyadenosine has the following formula:

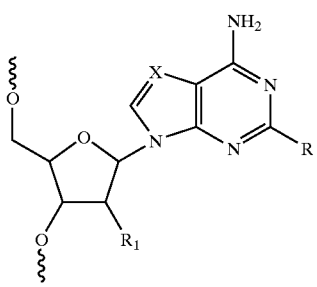

(IV)

in which $R_1$ is a hydrogen atom or an —OH group; R is a hydrogen atom or a $NH_2$ group; X is a nitrogen atom, or groups with the formula: C—Br, C—Cl, C—C≡CH, and C—C≡C—$CH_3$.

10. A hybridization complex in accordance with claim 9, wherein the modified deoxyadenosine of formula (IV) is chosen from among: 1'-amino-2-deoxyadenosine, 7-deaza-7-bromodeoxyadenosine, 7-deaza-7-propynyldeoxyadenosine, 1'-amino-2-7-deaza-7-bromodeoxyadenosine, and 1'-amino-2-7-deaza-7-propynyl-deoxyadenosine.

11. A method for assaying a nucleic acid sequence comprising:

copying all or part of the sequence to be assayed using a mixture of triphosphates of naturally-occurring and/or modified C and/or G nucleosides, and naturally-occurring A and T/U nucleosides, to prepare a first nucleic acid molecule, providing a second nucleic acid molecule which is a nucleic acid probe, contacting the first nucleic acid molecule with the second nucleic acid molecule under conditions allowing formation of a hybridisation complex, wherein at least one C or G base contained in the sequence of the first and/or second nucleic acid molecule, or at least one C and G base contained in the sequence of the first or second nucleic acid molecule, is a modified base which forms a modified C—G base pair upon hybridisation, such that the difference between the melting temperature of:
i.) the complex and
ii) the complex wherein in place of the modified base pair is a naturally-occurring A—T base pair
is less than the difference between the melting temperature of:
i) the complex wherein in the place of the modified base pair is a naturally-occurring C—G base pair and
ii) the complex wherein in the place of the modified base pair is a naturally-occurring A—T/U base pair, and assaying the hybridisation complex; or copying all or part of the sequence to be assayed using a mixture of triphosphates of naturally-occurring and/or modified A and/or T/U nucleosides, and naturally-occurring C and G nucleosides to prepare a first nucleic acid molecule, providing a second nucleic acid molecule which is a nucleic acid probe, contacting the first nucleic acid molecule with the second nucleic acid molecule under conditions allowing formation of a hybridisation complex, wherein at least one A or T/U base contained in the sequence of the first and/or second nucleic acid molecule, or at least one A and T/U base contained in the sequence of the first or second nucleic acid molecule, is a modified base which forms a modified A—T/U base pair upon hybridisation, such that the difference between the melting temperature of:
i.) the complex wherein in place of the modified base pair is a naturally-occurring C—G base pair and
ii) the complex
is less than the difference between the melting temperature of:
i) the complex wherein in the place of the modified base pair is a naturally-occurring C—G base pair and
ii) the complex wherein in the place of the modified base pair is a naturally-occurring A—T/U base pair, assaying the hybridisation complex; or copying all or part of the sequence to be assayed using a mixture of naturally-occurring and/or modified A and/or T/U bases and naturally-occurring and/or modified C and/or G bases to prepare a first nucleic acid molecule, providing a second nucleic acid molecule which is a nucleic acid probe, contacting the first nucleic acid molecule with the second nucleic acid molecule under conditions allowing formation of a hybridisation complex, wherein at least one C and/or G base and at least one A and/or T/U base contained in the sequence of the first or second nucleic acid molecule is a modified base, or wherein at least one A or T/U base and at least one C or G base contained in the sequence of the first and second nucleic acid molecule is a modified base, wherein the melting temperature of the complex is between:
(i) the melting temperature of the complex wherein in place of the modified C—G base pair and modified A—T/U base pair are naturally-occurring C—G base pairs, and
ii) the melting temperature of the complex wherein in place of the modified C—G base pair and modified A—T/U base pair are naturally-occurring A—T/U base pairs assaying the hybridisation complex.

12. A method for the assay of the sequence of a nucleic acid in accordance with claim 11, wherein the nucleic acid probe is an oligonucleotide having 9 to 30 nucleosides.

13. A method for assaying a nucleic acid sequence in accordance with claim 11 wherein the nucleic acid probe is suitable for sequencing or detecting point mutations.

14. A method for assaying the sequence of a nucleic acid molecule in accordance with claim 11, wherein one of the types of bases contained in the composition of said first and/or second nucleic acid molecule is a modified deoxycytidine having the following formula:

(I)

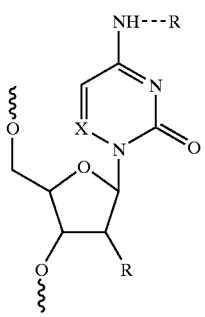

in which R is selected from the group consisting of a hydrogen atom, an alkyl group at $C_1$ to $C_5$, an allyl group, and a propargyl group; R1 is a hydrogen atom or an —OH group; and X is a nitrogen atom or a —CH— group.

15. A method for assaying the sequence of a nucleic acid molecule in accordance with claim 11, wherein one of the base types contained in the composition of said first and/or second nucleic acid molecule is a modified deoxyguanosine having the following formula:

(II)

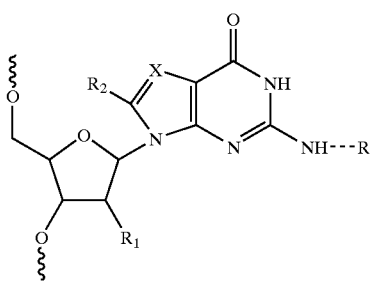

in which R is selected from the group consisting of a hydrogen atom, an alkyl group at $C_1$ to $C_5$, an allyl group, and a propargyl group; $R_1$ is a hydrogen atom or an —OH group; $R_2$ a hydrogen atom or a bromine atom; and X is a nitrogen atom or a —CH— group.

16. A method for assaying the sequence of a nucleic acid molecule in accordance with claim 11, wherein one of the types of bases contained in the composition of said first and/or second nucleic acid molecule is a modified deoxyuridine having the following formula:

(III)

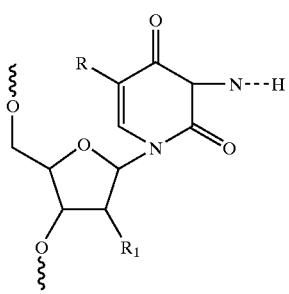

in which $R_1$ is a hydrogen atom or an —OH group; R is a group with the formula of —C≡CH, or —C≡C—$CH_3$.

17. A method for assaying the sequence of a nucleic acid molecule in accordance with claim 11 wherein one of the types of bases contained in the composition of said first and/or second nucleic acid molecule is a modified deoxyadenosine having the following formula:

(IV)

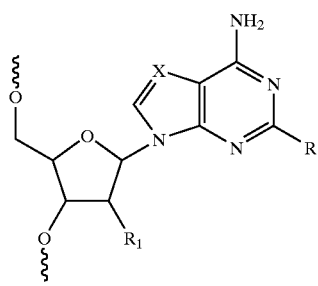

in which $R_1$ is a hydrogen atom or an —OH group; R is a hydrogen atom or a $NH_2$ group; X is a nitrogen atom, or groups with the formula: C—Br, C—Cl C—C≡CH, or C—C≡C—$CH_3$.

18. A method for assaying the sequence of a nucleic acid molecule in accordance with claim 11, wherein the contacting of the first and second nucleic acid molecules under conditions allowing the formation of a hybridisation complex is conducted in the presence of tetramethylammonium chloride or trimethylammonium halide.

19. A method for producing a hybridisation complex which comprises at least one modified C—G base pair comprising:

contacting a first nucleic acid molecule with a second nucleic acid molecule under conditions allowing formation of a hybridisation complex, wherein at least one C or G base contained in the sequence of the first and/or second nucleic acid molecule, or at least one C and G contained in the sequence of the first or second nucleic acid molecule, is a modified base which forms a modified C—G base pair upon hybridisation, such that the difference between the melting temperature of:
   i.) the complex and
   ii) the complex wherein in place of the modified base pair is a naturally-occurring A—T base pair
is less than the difference between the melting temperature of:
   the complex wherein in the place of the modified base pair is a naturally-occurring C—G base pair and
   ii) the complex wherein in the place of the modified base pair is a naturally-occurring A—T/U base pair,
wherein the hybridisation complex is produced.

20. A method for producing a hybridisation complex which comprises at least one modified A—T/U base pair, comprising:

contacting a first nucleic acid molecule with a second nucleic acid molecule under conditions allowing formation of a hybridisation complex, wherein at least one A or T/U base contained in the sequence of the first and/or second nucleic acid molecule, or at least one A and T/U base contained in the sequence of the first or second nucleic acid molecule, is a modified base which forms a modified A—T/U base pair upon hybridisation, such that the difference between the melting temperature of:
   i.) the complex wherein in place of the modified base pair is a naturally-occurring C—G base pair and ii) the complex is less than the difference between the melting temperature of:

i) the complex wherein in the place of the modified base pair is a naturally-occurring C—G base pair and
ii) the complex wherein in the place of the modified base pair is a naturally-occurring A—T/U base pair, wherein the hybridisation complex is produced.

21. A method for producing a hybridisation complex which comprises at least one modified C—G base pair and at least one modified A—T/U base pair, comprising:

contacting a first nucleic acid molecule with a second nucleic acid molecule under conditions allowing formation of a hybridisation complex, wherein at least one C and/or G base and at least one A and/or T/U base contained in the sequence of the first or second nucleic acid molecule is a modified base, or wherein at least one A or T/U base and at least one C or G base contained in the sequence of the first and second nucleic acid molecule is a modified base, wherein the melting temperature of the complex is between:

the melting temperature of the complex wherein in place of the modified C—G base pair and modified A—T/U base pair are naturally-occurring C—G base pairs, and
ii) the melting temperature of the complex wherein in place of the modified C—G base pair and modified A—T/U base pair are naturally-occurring A—T/U base pairs wherein the hybridisation complex is produced.

22. A method for producing a hybridisation complex in accordance with claim 19, 20 or 21, wherein the modified deoxycytidine has the following formula:

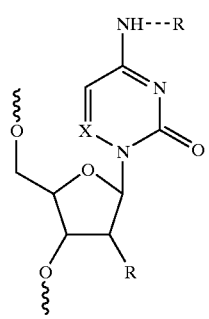

(I)

in which R is selected from the group consisting of a hydrogen atom, an alkyl group at $C_1$ to $C_5$, an allyl group, and a propargyl group; R1 is a hydrogen atom or an —OH group; and X is a nitrogen atom or a —CH— group.

23. A method in accordance with claim 22, wherein the modified cytidine of formula (I) is chosen from among: N-4-methyl-2'-deoxycytidine, N-4-ethyl-2'-deoxycytidine, N-4-propyl-2'-deoxycytidine, N-4-allyl-2'-deoxycytidine, N-4-propargyl-2'-deoxycytidine, 1-B-D-arabinofuranosyl-cytosine, and 6-azadeoxycytidine.

24. A method for producing a hybridisation complex in accordance with claim 19, 20 or 21, wherein the modified deoxyguanosine has the following formula:

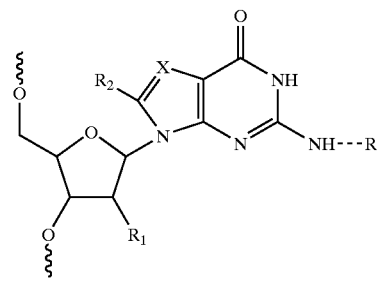

(II)

in which R is selected from the group consisting of a hydrogen atom, an alkyl group at $C_1$ to $C_5$, an allyl group, and a propargyl group; $R_1$ is a hydrogen atom or an —OH group; $R_2$ is a hydrogen atom or a bromine atom; and X is a nitrogen atom or a —CH— group.

25. A method in accordance with claim 24, wherein the modified guanosine of formula (II) is chosen from among: N-2-methyldeoxyguanosine, N-2-propyldeoxyguanosine, N-2-isopropyldeoxyguanosine, N-2-ethyldeoxyguanosine, 7-deazadeoxyguanosine, and 8-bromo-deoxyguanosine.

26. A method for producing a hybridisation complex in accordance with claim 19, 20 or 21, wherein the modified deoxyuridine has the following formula:

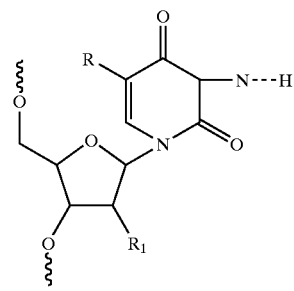

(III)

in which $R_1$ is a hydrogen atom or an —OH group; R is —C≡CH, or —C≡—$CH_3$.

27. A method in accordance with claim 26, wherein the modified deoxyuridine of formula (III) is chosen from among: 5-ethynyldeoxyuridine, and 5-propynyldeoxyuridine.

28. A method for producing a hybridisation complex in accordance with claim 19, 20 or 21, wherein the modified deoxyadenosine has the following formula:

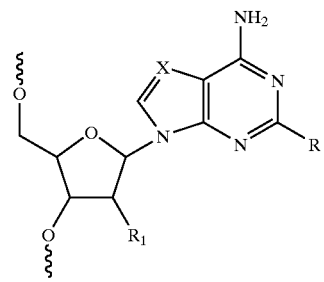

(IV)

in which $R_1$ is a hydrogen atom or an —OH group; R is a hydrogen atom or a $NH_2$ group; X is a nitrogen atom, or groups with the formula: C—Br, C—Cl, C—C≡CH, and C—C≡C—$CH_3$.

29. A method in accordance with claim 28, wherein the modified deoxyadenosine of formula (IV) is chosen from among: 1'-amino-2-deoxyadenosine, 7-deaza-7-bromodeoxyadenosine, 7-deaza-7-propynyldeoxyadenosine, 1'-amino-2-7-deaza-7-bromodeoxyadenosine, and 1'-amino-2-7-deaza-7-propynyl-deoxyadenosine.

30. A method in accordance with claim 19, 20 or 21 wherein the first and second nucleic acid molecules are of deoxyribonucleic type.

31. A method for producing a hybridisation complex in accordance with claim 19, 20 or 21, wherein the contacting of the first and second nucleic acid molecules under conditions allowing the formation of a hybridisation complex is conducted in the presence of tetramethylammonium chloride or trimethylammonium halide.

* * * * *